United States Patent
Katsuki et al.

(10) Patent No.: US 9,357,957 B2
(45) Date of Patent: Jun. 7, 2016

(54) MEASURING APPARATUS, MEASURING SYSTEM, ELECTRIC POWER SUPPLY APPARATUS, AND ELECTRIC POWER SUPPLY METHOD

(75) Inventors: Koji Katsuki, Kyoto (JP); Yasunori Shiraki, Kyoto (JP)

(73) Assignee: ARKRAY, Inc., Kyoto (JP)

(*) Notice: Subject to any disclaimer, the term of this patent is extended or adjusted under 35 U.S.C. 154(b) by 750 days.

(21) Appl. No.: 13/574,266

(22) PCT Filed: Jan. 17, 2011

(86) PCT No.: PCT/JP2011/050671
§ 371 (c)(1),
(2), (4) Date: Jul. 31, 2012

(87) PCT Pub. No.: WO2011/090003
PCT Pub. Date: Jul. 28, 2011

(65) Prior Publication Data
US 2012/0283968 A1  Nov. 8, 2012

(30) Foreign Application Priority Data
Jan. 21, 2010  (JP) ................. 2010-011161

(51) Int. Cl.
*G01R 21/00* (2006.01)
*A61B 5/1473* (2006.01)
*G01R 31/36* (2006.01)
*H01M 10/44* (2006.01)

(52) U.S. Cl.
CPC ............ *A61B 5/1473* (2013.01); *G01R 21/00* (2013.01); *G01R 31/36* (2013.01); *H01M 10/44* (2013.01); *Y10T 307/615* (2015.04)

(58) Field of Classification Search
USPC ........................................... 702/60
See application file for complete search history.

(56) References Cited

U.S. PATENT DOCUMENTS

| | | | |
|---|---|---|---|
| 4,627,840 A * | 12/1986 | Cuadra et al. ............... | 604/151 |
| 5,461,263 A | 10/1995 | Helfrich | |
| 6,424,847 B1 | 7/2002 | Mastrototaro et al. | |
| 6,809,653 B1 | 10/2004 | Mann et al. | |
| 6,895,263 B2 | 5/2005 | Shin et al. | |
| 7,029,444 B2 | 4/2006 | Shin et al. | |
| 7,157,723 B2 | 1/2007 | Colvin et al. | |
| 7,187,961 B2 | 3/2007 | Yamashita et al. | |

(Continued)

FOREIGN PATENT DOCUMENTS

| CN | 1780581 A | 5/2006 |
|---|---|---|
| EP | 2127598 A1 | 12/2009 |

(Continued)

OTHER PUBLICATIONS

International Preliminary Report on Patentability with Written Opinion issued in corresponding International Application No. PCT/JP2011/050671 mailed Aug. 16, 2012.

(Continued)

*Primary Examiner* — Paul D Lee
(74) *Attorney, Agent, or Firm* — Morgan, Lewis & Bockius LLP

(57) ABSTRACT

A technique is provided, which makes it possible to continuously supply the driving electric power stably to a sensor even when the continuous monitoring period ranges over a long period of time when the numerical information is measured in relation to a test substance contained in a sample.

8 Claims, 16 Drawing Sheets

(56) References Cited

U.S. PATENT DOCUMENTS

| | | |
|---|---|---|
| 7,227,156 B2 | 6/2007 | Colvin et al. |
| 7,405,387 B2 | 7/2008 | Colvin et al. |
| 7,755,022 B2 | 7/2010 | Colvin et al. |
| 7,800,078 B2 | 9/2010 | Colvin et al. |
| 7,890,295 B2 | 2/2011 | Shin et al. |
| 7,927,559 B2 | 4/2011 | Bodlaender et al. |
| 7,965,180 B2 | 6/2011 | Koyama |
| 7,976,478 B2 | 7/2011 | Fujiwara et al. |
| 2002/0161288 A1 | 10/2002 | Shin et al. |
| 2004/0100376 A1 | 5/2004 | Lye et al. |
| 2004/0206916 A1 | 10/2004 | Colvin et al. |
| 2004/0263354 A1 | 12/2004 | Mann et al. |
| 2005/0004439 A1 | 1/2005 | Shin et al. |
| 2005/0027177 A1 | 2/2005 | Shin et al. |
| 2005/0035304 A1 | 2/2005 | Colvin et al. |
| 2006/0001550 A1 | 1/2006 | Mann et al. |
| 2006/0007017 A1 | 1/2006 | Mann et al. |
| 2006/0092421 A1 | 5/2006 | Colvin et al. |
| 2006/0168464 A1 | 7/2006 | Yuasa |
| 2007/0102649 A1 | 5/2007 | Colvin et al. |
| 2007/0123756 A1 | 5/2007 | Kitajima et al. |
| 2007/0208244 A1 | 9/2007 | Brauker et al. |
| 2008/0001735 A1 | 1/2008 | Tran |
| 2008/0030369 A1 | 2/2008 | Mann et al. |
| 2008/0079565 A1 | 4/2008 | Koyama |
| 2008/0201055 A1* | 8/2008 | Maeda ........................ 701/102 |
| 2009/0001926 A1 | 1/2009 | Sato |
| 2009/0005666 A1 | 1/2009 | Shin et al. |
| 2009/0039286 A1 | 2/2009 | Colvin et al. |
| 2009/0146826 A1 | 6/2009 | Gofman et al. |
| 2009/0292167 A1 | 11/2009 | Kimoto |
| 2009/0312667 A1 | 12/2009 | Utsunomiya et al. |
| 2010/0004521 A1 | 1/2010 | Epps |
| 2010/0222849 A1 | 9/2010 | Forsell |
| 2010/0262039 A1 | 10/2010 | Fujiwara et al. |
| 2011/0228065 A1 | 9/2011 | Koyama |
| 2012/0029332 A1 | 2/2012 | Katsuki et al. |
| 2012/0179015 A1 | 7/2012 | Mann et al. |

FOREIGN PATENT DOCUMENTS

| | | |
|---|---|---|
| JP | 2002-085556 | 3/2002 |
| JP | 2004-024551 | 1/2004 |
| JP | 2005-524463 | 8/2005 |
| JP | 2005-287762 | 10/2005 |
| JP | 2006-507078 | 3/2006 |
| JP | 2006-280464 | 10/2006 |
| JP | 2006-523843 | 10/2006 |
| JP | 2007-105316 | 4/2007 |
| JP | 2007-225444 | 9/2007 |
| JP | 2008-109847 | 5/2008 |
| JP | 2008-161641 | 7/2008 |
| JP | 2008-167828 | 7/2008 |
| JP | 2008-237099 | 10/2008 |
| JP | 2009-093948 | 4/2009 |
| JP | 2009-536065 | 10/2009 |
| JP | 2009-536441 | 10/2009 |
| JP | 4485568 | 4/2010 |
| WO | 00/19887 A1 | 4/2000 |
| WO | 2005/015163 A2 | 2/2005 |
| WO | 2007/096720 A1 | 8/2007 |
| WO | WO 2007/108518 | 9/2007 |
| WO | 2009/051536 A1 | 4/2009 |
| WO | WO 2010/106781 | 9/2010 |

OTHER PUBLICATIONS

International Search Report issued in corresponding International Application No. PCT/JP2011/050671 dated Feb. 8, 2011.

Office Action issued in corresponding Chinese Patent Application No. 201180006538.8 dated Mar. 10, 2015.

Partial Supplementary European Search Report issued in corresponding European Patent Application No. 11734609.8 dated Dec. 18, 2015.

Extended European Search Report issued in corresponding European Patent Application No. 11734609.8 dated Apr. 11, 2016.

* cited by examiner

MEASURING APPARATUS, MEASURING SYSTEM, ELECTRIC POWER SUPPLY APPARATUS, AND ELECTRIC POWER SUPPLY METHOD

CROSS-REFERENCE TO RELATED APPLICATION

This application is the U.S. National Phase under 35 U.S.C. §371 of International Application PCT/JP2011/050671, filed on Jan. 17, 2011, which claims priority to JP Application No. 2010-011161, filed on Jan. 21, 2010, the contents of which are herein incorporated by reference in their entireties.

TECHNICAL FIELD

The present invention relates to a measuring apparatus for measuring numerical information in relation to a test substance (a target substance) contained in a sample, a measuring system, an electric power supply apparatus, and an electric power supply method.

BACKGROUND ART

Conventionally, a technique is known, in which an electrochemical sensor implanted, for example, in belly (abdomen) or arm of an examinee is utilized to continuously measure the numerical information in relation to a test substance contained in a body fluid, for example, the glucose concentration (so-called blood sugar level or blood glucose level) in an interstitial fluid of the examinee. The electrochemical sensor is a sensor capable of detecting a minute amount of current by utilizing the electrochemical reaction, which is suitable for the detection of a minute amount of chemical substance that causes an oxidation reduction reaction.

A biosensor, in which an enzyme is immobilized to a sensor unit to be arranged while being implanted subcutaneously beneath the skin and the enzyme reaction thereof is utilized to detect a test substance contained in a sample, is used in many cases as the electrochemical sensor for measuring the glucose concentration. Usually, the biosensor of this type has a working electrode and a counter electrode, and the enzyme (for example, glucose oxidase) is immobilized to the working electrode. A voltage is applied between the working electrode and the counter electrode, and the glucose concentration can be measured on the basis of a response current obtained thereby.

The glucose oxidase produces gluconic acid by selectively reacting on the glucose under an existence of oxygen. On this occasion, the oxygen is reduced, while hydrogen peroxide proportional to a quantity of the glucose is generated. The hydrogen peroxide can be oxidized electrochemically easily and can be therefore measured by use of a pair of electrodes. Namely, the response current value can be obtained by the electrochemically oxidizing the hydrogen peroxide generated by the enzyme reaction of the enzyme as described above. Then, the glucose concentration can be calculated based on a sampling current obtained by periodically sampling the electric current from the continuously acquired response current values.

The measuring apparatus, which is provided to continuously measure the test substance contained in the sample, for example, the glucose concentration or the like as described above, is used in many cases for the way of use of the so-called continuous monitoring (measurement) in which the glucose concentration is measured in succession over a somewhat long period of time. The continuous monitoring as described above has the following advantage. That is, the glucose concentration can be measured automatically and continuously in succession, for example, even when an examinee (user) is asleep. It is possible to always monitor the blood sugar level (blood glucose level) of the examinee.

Conventionally, a driving source, which is provided to drive such a glucose continuous monitoring apparatus, uses the electric power of a primary battery (so-called dry battery or the like) in many cases (see, for example, Patent Document 1). It is a matter of course that the measuring apparatus cannot be driven when the electric power energy of the primary battery is discharged and exhausted. Therefore, it is necessary that the primary battery should be exchanged with a new primary battery.

PRIOR ART DOCUMENTS

Patent Document

Patent Document 1: JP2005-524463A.

SUMMARY OF THE INVENTION

Problems to be Solved by the Invention

However, it is inconvenient that the monitoring of the test substance is interrupted even temporarily in the measuring apparatus for measuring the numerical information in relation to the test substance contained in the sample as in the glucose continuous monitoring apparatus. For example, a patient of diabetes tends to be in hypoglycemia when the patient is asleep. If the monitoring performed by the measuring apparatus is interrupted in such a circumstance, a situation is consequently caused such that it is impossible to give, for example, any notice and/or warning of the fact that the glucose concentration exhibits an abnormal value.

The present invention has been made taking the forgoing actual circumstances into consideration. An object of the present invention is to provide a technique which makes it possible to continuously supply the driving electric power stably to a sensor even when the continuous monitoring period ranges over a long period of time when the numerical information is measured in relation to a test substance contained in a sample.

Means for Solving the Problems

In order to solve the problem as described above, the present invention adopts the following means.

That is, the measuring apparatus according to the present invention resides in a measuring apparatus for continuously measuring numerical information in relation to a test substance contained in a sample; the measuring apparatus comprising a sensor which continuously generates a signal correlated with the numerical information in relation to the test substance contained in the sample; and an electricity accumulating unit which is charged by an electric power supplied from a power generating unit for generates the electric power for driving the sensor and which supplies the accumulated electric power to the sensor.

According to the present invention, even when the continuous monitoring period ranges over a long period of time, the driving electric power can be continuously supplied stably to the measuring apparatus. Thus, it is possible to suppress such an inconvenience that the measurement of the numerical information in relation to the test substance contained in the sample is interrupted during the continuous monitoring period. The term "continuously" described above resides in a concept which includes such a mode that the sensor generates the signal correlated with the numerical information in relation to the test substance intermittently while providing constant or indefinite time intervals. In this specification, the continuous monitoring period refers to the duration period in which the continuous (intermittent) monitoring or measurement of the numerical information in relation to the test substance contained in the sample is performed continuously or in succession. In this specification, the "charging" and the "accumulation" are used synonymously, and the "electricity accumulating unit" resides in a concept including an electricity accumulating device (for example, so-called condenser, capacitor and the like) and a storage battery (for example, so-called secondary battery and the like).

The measuring apparatus according to the present invention may be an apparatus which is used by being attached to an examinee. The sensor according to the present invention may have a sensor unit which is arranged while being embedded subcutaneously beneath the skin and which is provided to detect the test substance contained in the body fluid. The sensor may be an electrochemical sensor which continuously generates or produces the electric signal correlated with the numerical information in relation to the test substance contained in the sample. The sensor unit may be formed, for example, on a part of a substrate or base member, on which a biological material such as an enzyme or the like may be retained to cause an enzyme reaction with respect to the test substance contained in the sample.

The electricity accumulating unit may supply the accumulated electric power to the sensor when a power supply request to supply the electric power to the sensor (electric power supply request) is given. The power supply request is such a request that the driving electric power should be supplied to the sensor, and the power supply request is given at every timing for measuring the numerical information in relation to the test substance by means of the sensor. The measurement timing may reside in a predetermined constant interval (for example, about several minutes), or the measurement timing may be given in accordance with a predetermined action performed by a user (for example, depression of a measurement start button).

The test substance contained in the sample can be exemplified, for example, by glucose and lactic acid contained in the body fluid. The numerical information in relation to the test substance resides in a concept which includes the numerical information for quantitatively evaluating the test substance such as the concentration, the amount and the like of the test substance, as well as the numerical information for qualitatively evaluating the test substance, for example, such that it is judged whether or not a certain test substance exists in a detection objective area and/or whether or not a certain test substance exceeds a certain level. It is also allowable that the body fluid is a body fluid of any animal other than human.

In the present invention, the power generating unit can generate the electric power in accordance with the action of the electromagnetic induction by utilizing the vibrational energy allowed to act in an environment of use. In this case, the power generating unit, which generates the electric power in accordance with the action of the electromagnetic induction, can be constructed to include an electromagnetic induction coil and a permanent magnet provided so that the relative positional relationship is changed depending on the vibrational energy.

Alternatively, the power generating unit can generate the electric power by performing the piezoelectric conversion by utilizing the pressure or the vibrational energy allowed to act in an environment of use. In this case, the power generating unit, which generates the electric power by performing the piezoelectric conversion, can be constructed to include a piezoelectric element (so-called piezo-element).

Further alternatively, the power generating unit can generate the electric power by performing the thermoelectric conversion by utilizing the temperature difference between the body temperature of an examinee and the environmental temperature brought about in an environment of use. In this case, the power generating unit, which generates the electric power by performing the thermoelectric conversion, can be constructed to include a Seebeck element. The Seebeck element is a thermoelectric conversion element capable of generating the electric power by utilizing the so-called Seebeck effect.

Further alternatively, the power generating unit can generate the electric power by performing the photoelectric conversion by utilizing the light energy received in an environment of use. In this case, the power generating unit, which generates the electric power by performing the photoelectric conversion, can be constructed to include a silicon solar cell or a dye-sensitized solar cell.

Further alternatively, the power generating unit may have a fuel cell, and the electric power can be generated by using the fuel cell. In this case, the fuel cell may use sugar or alcohol as fuel.

The electricity accumulating unit may be constructed to include at least any one of an electric double-layer capacitor and a secondary battery. In this case, the secondary battery may be, for example, a lithium ion secondary battery.

The measuring apparatus according to the present invention may further comprise a sensor control unit which controls the sensor and which calculates the numerical information in relation to the test substance on the basis of a signal generated by the sensor, wherein the electricity accumulating unit can also supply the accumulated electric power to the sensor by the aid of the sensor control unit. In this arrangement, the power generating unit and the electricity accumulating unit may be installed respectively in a casing which accommodates the sensor control unit.

The measuring apparatus may further comprise a result display unit which acquires a calculation result brought about by the sensor control unit and which displays the calculation result. In this arrangement, the power generating unit and the electricity accumulating unit may be installed respectively in a casing which accommodates the sensor control unit or a casing in which the result display unit is provided. The test substance of the present invention may be glucose contained in blood or interstitial fluid. The measuring apparatus may measure a concentration of glucose.

In a more preferred aspect, the measuring apparatus according to the present invention resides in a measuring apparatus for measuring numerical information in relation to a test substance contained in a sample; the measuring apparatus comprising a sensor which continuously generates a signal correlated with the numerical information in relation to the test substance contained in the sample; a power generating unit which generates an electric power for driving the sensor; an electricity accumulating unit which is charged by the electric power supplied from the power generating unit and which supplies the accumulated electric power to the sensor; and a power generation control unit which monitors a power generation amount generated by the power generating unit.

In the measuring apparatus according to the present invention, the power generation control unit may start the monitoring of the power generation amount in the power generating unit if a voltage value of the electric power accumulated in the electricity accumulating unit is not more than a reference voltage for judgment. The power generation control unit may calculate a power generation rate as the power generation amount per unit time in the power generating unit when the power generation amount generated by the power generating unit is monitored. The measuring apparatus may further comprise a warning unit which outputs a predetermined warning if the power generation rate calculated by the power generation control unit is not more than a predetermined reference power generation rate.

The measuring apparatus according to the present invention may further comprise an emergency power source; wherein an electric power is supplied from the emergency power source to the electricity accumulating unit if the power generation rate calculated by the power generation control unit is not more than a predetermined reference power generation rate. The power generating unit may be constructed to include a plurality of power generating devices; and the power generation control unit may increase a number of the power generating devices to be operated if the calculated power generation rate is lower than a predetermined reference power generation rate. The power generating unit may be constructed to include a plurality of types of power generating devices based on different power generation systems; and the power generation control unit may change the power generating device to be operated from the power generating device in operation to the power generating device of another type based on the different power generation system if the calculated power generation rate is not more than a predetermined reference power generation rate.

The measuring apparatus according to the present invention may further comprise a storage unit which stores the power generation rate calculated by the power generation control unit; wherein the power generation control unit regulates a value of a reference voltage for judgment which is a threshold value to start the monitoring of the power generation amount in the power generating unit depending on an average power generation rate calculated by averaging values of the power generation rates obtained in past a plurality of times including a value stored most recently, of the power generation rates stored in the storage unit.

In another aspect, the present invention can be grasped as a measuring system for continuously measuring numerical information in relation to a test substance contained in a sample, an electric power supply apparatus for supplying an electric power to a sensor (for example, an electrochemical sensor), and an electric power supply method.

That is, the measuring system according to the present invention resides in a measuring system for continuously measuring numerical information in relation to a test substance contained in a sample; the measuring system comprising a sensor which continuously generates a signal correlated with the numerical information in relation to the test substance contained in the sample; a power generating unit which generates an electric power for driving the sensor; an electricity accumulating unit which is charged by the electric power supplied from the power generating unit and which supplies the accumulated electric power to the sensor; and a power generation control unit which monitors a power generation amount generated by the power generating unit.

The electric power supply apparatus according to the present invention resides in an electric power supply apparatus for supplying an electric power to a sensor for continuously generating a signal correlated with numerical information in relation to a test substance contained in a sample; the electric power supply apparatus comprising a power generating unit which generates the electric power for driving the sensor; an electricity accumulating unit which is charged by the electric power supplied from the power generating unit and which supplies the accumulated electric power to the sensor; and a power generation control unit which monitors a power generation amount generated by the power generating unit.

The electric power supply method according to the present invention resides in an electric power supply method for supplying an electric power to a sensor for continuously generating a signal correlated with numerical information in relation to a test substance contained in a sample; the electric power supply method comprising a power generating step of generating the electric power for driving the sensor; a power generation amount monitoring step of monitoring a power generation amount generated by a power generating unit; a charging step of performing charging with the electric power generated in the power generating step; and a supplying step of supplying the electric power accumulated in the charging step to the sensor. In the power generating step, the electric power for driving the sensor may be generated by utilizing at least any one of the action of the electromagnetic induction which utilizes the vibrational energy allowed to act in an environment of use, the piezoelectric effect which utilizes the pressure or the vibrational energy allowed to act in an environment of use, the thermoelectric effect which utilizes the temperature difference between two different portions in an environment of use, and the photoelectric effect which utilizes the light energy received in an environment of use.

The means for solving the problem according to the present invention can be combined with each other as far as possible. For example, the various types of the power generating units and the various types of the electricity accumulating units, which are exemplified by way of example when the measuring apparatus according to the present invention is explained, can be preferably applied to the measuring system, the electric power supply apparatus, and the electric power supply method described above respectively.

Effect of the Invention

According to the present invention, it is possible to provide the technique which makes it possible to continuously supply the driving electric power stably to the sensor even when the continuous monitoring period ranges over a long period of time when the numerical information is measured in relation to a test substance contained in a sample.

MODE FOR CARRYING OUT THE INVENTION

An explanation will be made exemplarily in detail below about a mode for carrying out the invention with reference to the drawings. In an embodiment of the present invention, an explanation will be made principally about a measuring apparatus (measuring system) which is used while being attached to an examinee.

First Embodiment

Figure 1:
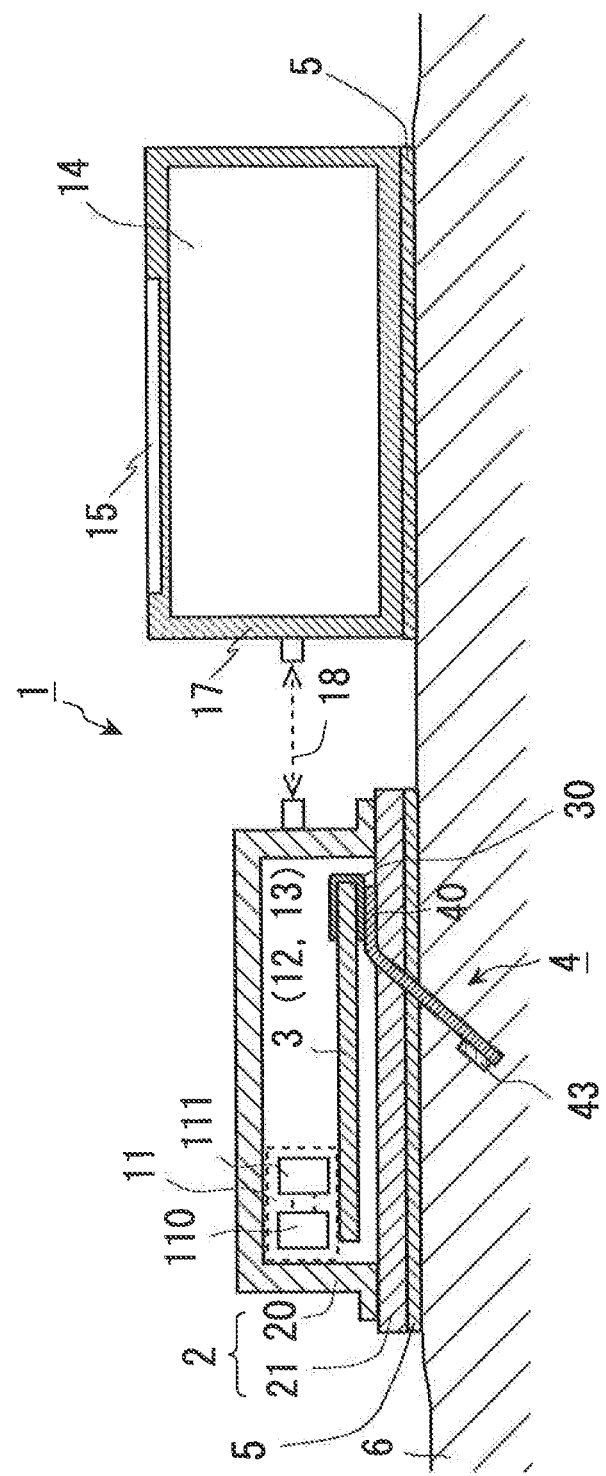
FIG. 1 shows a schematic arrangement of a measuring apparatus according to a first embodiment.

FIG. 1 shows a schematic arrangement of a measuring apparatus (measuring system) 1 according to a first embodiment. The measuring apparatus 1 is a glucose continuous measuring apparatus which is capable of measuring the glucose concentration in interstitial fluid continuously and automatically. The measuring apparatus 1 is used, for example, such that the measuring apparatus 1 is installed to the skin of belly (abdomen) or arm of human body (examinee). The measuring apparatus 1 is provided with a casing (housing) 2, a control computer 3, and an electrochemical sensor 4. An explanation will be made in this section about an example in which the glucose concentration in interstitial fluid is measured by means of the measuring apparatus 1. However, it is of course allowable that the glucose concentration in blood is measured. Components or parts, which are the same as or equivalent to components or part depicted in the drawing referred to previously, are designated by the same reference numerals in the drawing referred to later on. The explanation of respective embodiments of the measuring apparatus according to the present invention referred to below also holds as the explanation of respective embodiments of the measuring system, the electric power supply apparatus, and the electric power supply method according to the present invention. In particular, when the present invention is grasped as the measuring system, the "measuring apparatus" referred to in the following explanation may be read and replaced with the "measuring system". In this case, it is assumed that the reference numeral "1" in each of the drawings indicates the "measuring system".

The electrochemical sensor 4 is a sensor for detecting a specified test substance by utilizing an electrochemical reaction. In this embodiment, a so-called biosensor is adopted as the electrochemical sensor 4. The biosensor is a sensor to continuously measure and detect a test substance by using an organism or a material originating from an organism as an element for recognizing the test substance. In this embodiment, the electrochemical sensor 4 is used to continuously measure the glucose concentration in body fluid, which is hereinafter referred to as "glucose sensor". In this embodiment, glucose contained in a body fluid corresponds to the test substance according to the present invention, and the glucose concentration can be exemplified as an example of the numerical information in relation to the test substance according to the present invention.

The casing 2 forms an outer shape of the measuring apparatus 1, and the casing 2 includes a cover 20 and a substrate 21. The cover 20 and the substrate 21 are mutually fixed to one another, and the control computer 3 is accommodated in the space defined by the cover 20 and the substrate 21. It is preferable that the casing 2 has the waterproof performance or the water resistant performance. The casing 2 as described above is obtained, for example, such that at least the cover 20 (and the substrate 21, if necessary) is formed of a material having extremely low water permeability such as metal, polypropylene resin or the like.

The substrate 21 is a portion through which the glucose sensor 4 is inserted. The substrate 21 fixes an end portion (hereinafter referred to as "proximal end portion") 40 disposed on the proximal end side of the glucose sensor 4. An adhesive film 5 is fixed to the substrate 21. The adhesive film 5 is utilized when the measuring apparatus 1 is fixed to the skin. A tape, which has the stickiness on both surfaces, can be used as the adhesive film 5.

The control computer 3 carries electronic parts required for predetermined operations of the measuring apparatus 1 (for example, application of voltage and calculation of glucose concentration). The control computer 3 further includes a terminal 30 which is provided to make contact with an electrode 42 (see FIG. 2) of the glucose sensor 4 described later on. The terminal 30 is utilized in order to obtain the response current value from the glucose sensor 4 by applying the voltage to the glucose sensor 4.

The glucose sensor 4 is provided to obtain the response corresponding to the glucose concentration in the interstitial fluid. An immobilized enzyme unit 43, which serves as the sensor unit for detecting glucose contained in the interstitial fluid, is formed at the forward end portion of the glucose sensor 4, although details will be described later on. At least the immobilized enzyme unit 43 is used while being implanted subcutaneously beneath the skin. In this arrangement, the glucose sensor 4 has an end portion 40 which protrudes from the skin 6 to make contact with the terminal 30 of the control computer 3. Further, a greater part of the glucose sensor 4 other than the above (including the immobilized enzyme unit 43 as well) is inserted into the skin 6.

Figure 2:
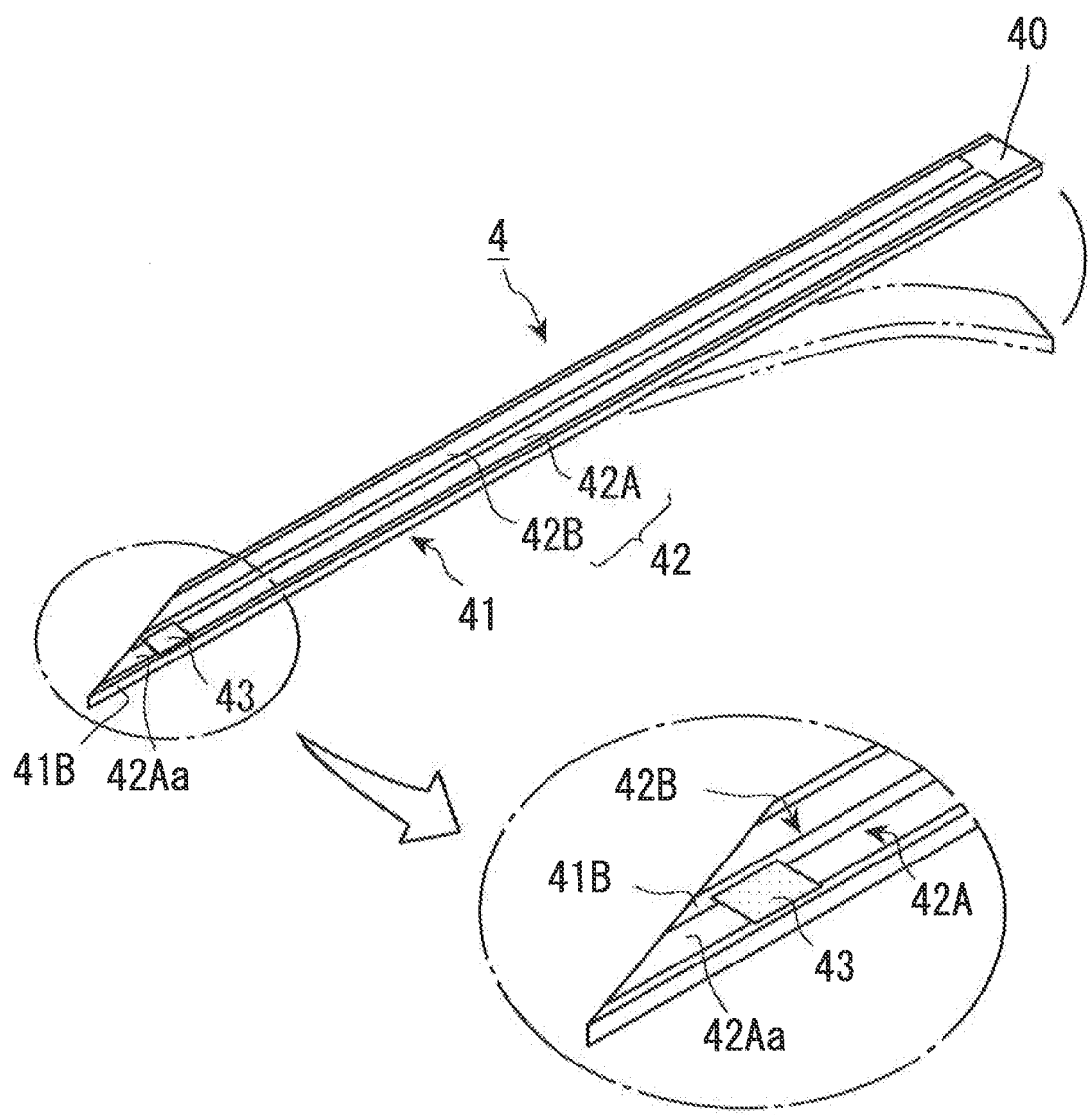
FIG. 2 shows a perspective view illustrating an entire glucose sensor according to the first embodiment together with an enlarged view of main components.

FIG. 2 shows a perspective view illustrating the entire glucose sensor 4 together with an enlarged view of main components. As shown in the drawing, the glucose sensor 4 has a substrate 41, electrodes 42, and the immobilized enzyme unit 43. The substrate 41 is provided to support the electrodes 42, which is formed to have a sheet-shaped form having the insulation performance and the flexibility. As for the substrate 41, an end portion 40 exists at the inside of the casing 2, while an end portion 41B is formed to have a sharp or acute shape. When the end portion 41B has the sharp structure, then it is possible to easily perform the insertion of the glucose sensor 4 into the skin 6, and it is possible to reduce the pain of a user.

It is appropriate that the material for the substrate 41 is not harmful for the human body and the material has the appropriate insulation performance. It is possible to use, for example, thermoplastic resins including, for example, polyethylene terephthalate (PET), polypropylene (PP), and polyethylene (PE), and thermosetting resins including, for example, polyimide resin and epoxy resin.

The electrodes 42 are utilized in order to take out electrons from the immobilized enzyme unit 43 by applying the voltage to the immobilized enzyme unit 43. The electrodes 42 include a working electrode 42A and a counter electrode 42B. The working electrode 42A is a portion to give and receive the electrons with respect to glucose. The counter electrode 42B is utilized to apply the voltage together with the working electrode 42A. The electrodes 42 can be formed by means of the screen printing by using carbon ink.

The immobilized enzyme unit 43 mediates the action to give and receive the electrons between glucose and the working electrode 42A. The immobilized enzyme unit 43 is formed on one surface of the substrate 41. The immobilized enzyme unit 43 is formed by immobilizing glucose oxidoreductase to an end portion 42Aa of the working electrode 42A.

It is possible to use, for example, glucose oxidase (GOD) and glucose dehydrogenase (GDH) as the glucose oxidoreductase. However, it is preferable to use GDH as the glucose oxidoreductase. In particular, it is preferable to use cytochrome GDH. When GDH is used as the glucose oxidoreductase, the electrons can be taken out from glucose without producing hydrogen peroxide. Therefore, it is possible to avoid any damage exerted by hydrogen peroxide on glucose and biological cells. It is possible to realize the glucose sensor 4 which is safer to the human body, which scarcely suffers from deterioration of the enzyme, and which has the high stability. As for the method for immobilizing the glucose oxidoreductase, it is possible to adopt various known methods including, for example, methods to utilize polymerizable gel, high molecular weight compounds such as polyacrylamide, phosphorus and the like, MPC polymer obtained by introducing silane coupling agent into phospholipid polymer, and protein film.

The measuring apparatus 1 is provided with an electric power supply device 11 which is a power source device for supplying the driving electric power to the glucose sensor 4. The electric power supply device 11 has a power generating unit 110 and an electricity accumulating unit (also referred to as "charging unit" in another way) 111, details of which will be described later on. The measuring apparatus 1 further includes a display unit component 14. The display unit component 14 acquires the calculation result of the glucose concentration calculated by a sensor control unit 12 as described later on, and the display unit component 14 displays the calculation result. As shown in FIG. 1, the display unit component 14 has a display panel 15 to display the calculation result of the glucose concentration. A casing 17 of the display unit component 14 is fixed to the skin by means of, for example, an adhesive film 5 in the same manner as the casing 2. The display unit component 14 is not an essential part or component for constructing the measuring apparatus 1 according to this embodiment.

Figure 3:
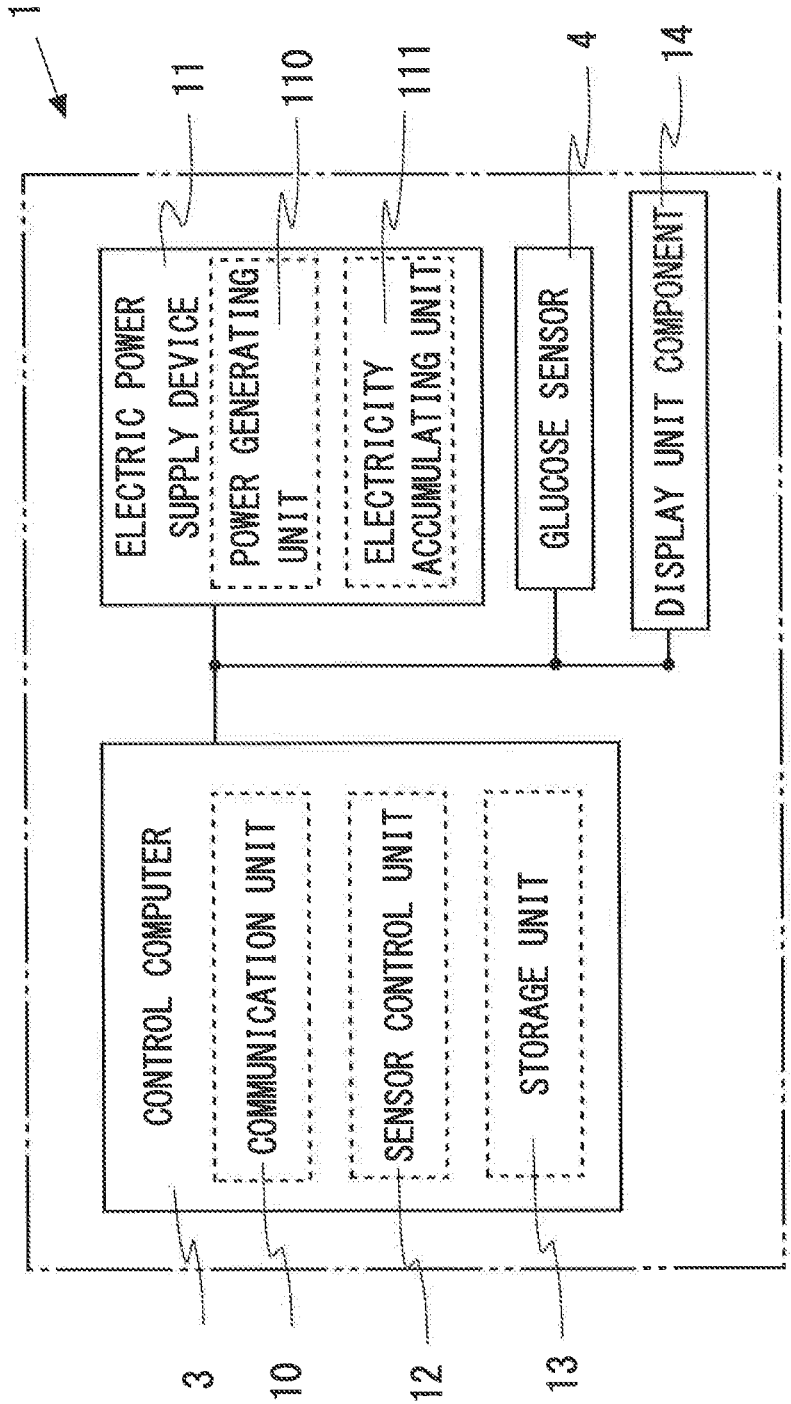
FIG. 3 shows a block diagram illustrating main components of the measuring apparatus according to the first embodiment.

FIG. 3 shows a block diagram illustrating main components of the measuring apparatus 1. In the drawing, a communication unit 10, a sensor control unit 12, and a storage unit 13, which are included in the control computer 3, are the functions realized by the control computer 3. The control computer 3 is a computer comprising, for example, a general purpose or exclusive processor which controls the respective functional units by processing the commands and the data, ROM (Read Only Memory) in which various control programs are stored, RAM (Random Access Memory) in which the control programs are developed, and a hard disk which stores various pieces of data to be used by the measuring apparatus 1, if necessary. The processor interprets and executes the control program developed in RAM. The components as described above may be provided individually respectively for the respective functional units including the processor, or the components as described above may be shared by the respective functional units. As shown in FIG. 3, the communication unit 10, the sensor control unit 12, and the storage unit 13 are realized in the control computer 3.

The sensor control unit 12 controls various operations including, for example, the timing of the voltage application, the applied voltage value, the sampling of the response current, the calculation of the glucose concentration, and the communication with an external information processing terminal.

The communication unit 10 is provided to perform the data communication with the display unit component 14. The communication unit 10 transmits, to the display unit component 14, the calculation result of the glucose concentration brought about by the sensor control unit 12. In this embodiment, the communication unit 10 performs the data communication in a wired manner by using a cable 18. However, it is possible to utilize any wireless communication means (for example, IrDA based on the use of infrared ray and Bluetooth based on the use of frequency band of 4 GHz).

The communication unit 10 realizes the function to perform the data communication with respect to the external information processing terminal. The external information processing terminal can be exemplified, for example, by an insulin injector or injecting device (for example, an insulin pump) for administering insulin to an examinee, a simple type blood sugar level measuring apparatus, a personal computer, and a warning apparatus. The warning apparatus is an apparatus which informs a patient of, for example, such a state that the examinee is in hypoglycemia, in hyperglycemia, almost in hypoglycemia, or almost in hyperglycemia, on the basis of the data supplied from the measuring apparatus 1.

The data communication between the measuring apparatus 1 and the insulin injector is performed, for example, such that the measurement result of the glucose concentration obtained by the measuring apparatus 1 is transmitted to the insulin injector. Accordingly, it is possible to control the insulin amount to be administered to the human body.

The data communication between the measuring apparatus 1 and the simple type blood sugar level measuring apparatus is performed, for example, such that the blood sugar level measurement result obtained by the simple type blood sugar level measuring apparatus is transmitted to the measuring apparatus 1. Accordingly, if the measurement result of the measuring apparatus 1 is compared with the measurement result obtained by the simple type blood sugar level measuring apparatus, and the measuring results are deviated from each other by not less than a certain value, then it is also allowable that the measuring apparatus 1 is calibrated. It is also appropriate that the intact data (response current), which is measured by the measuring apparatus 1, is transmitted to the simple type blood sugar level measuring apparatus.

The data communication between the measuring apparatus 1 and the personal computer is performed, for example, such that the blood sugar level measurement result or the intact data (response current) of the measuring apparatus 1 is transmitted to the personal computer. Accordingly, the personal computer can monitor the transition and the change of the glucose concentration.

The storage unit 13 stores the programs and the data required for the various types of calculation (for example, the data in relation to the calibration curve and the data in relation to the voltage application pattern). The storage unit 13 may be capable of further storing the response current value supplied from the glucose sensor 4 and the calculated glucose concentration.

In this arrangement, the electric power supply device 11 is accommodated in the casing 2 in the same manner as the control computer 3 for constructing the sensor control unit 12 as shown in FIG. 1. The electricity accumulating unit 111, which is provided in the electric power supply device 11, is a so-called secondary battery (storage battery or storage cell). The electricity accumulating unit 111 functions such that the electric power, which is supplied by the power generating unit 110 as described later on, is accumulated beforehand by means of the charging (i.e., electricity is accumulated), and the accumulated electric power is supplied to the glucose sensor 4. In this embodiment, the power generating unit 110 is constructed to include a lithium ion secondary battery. As well-known in relation to the lithium ion secondary battery, for example, a lithium oxide is used for the positive pole (electrode), and a carbon material is used for the negative pole (electrode). During the charging (electricity accumulation), the lithium ion is separated from the positive pole, and the lithium ion is moved to the negative pole side through an electrolyte and a separator. During the discharge, the lithium ion, which is accumulated in the carbon material, is moved to the positive pole side, and the lithium ion returns to the lithium oxide. The electricity accumulating unit 111 of this embodiment can be also constructed to include other various secondary batteries including, for example, nickel-cadmium secondary battery and nickel-hydrogen secondary battery. The electricity accumulating unit 111 may be an electricity accumulating device or accumulator (also referred to as "condenser" or "capacitor"). It is also preferable that the electricity accumulating unit 111 is constructed to include, for example, an electric double-layer capacitor (EDLC). The electric double-layer capacitor is such a capacitor that the electricity accumulating efficiency is remarkably enhanced by utilizing the physical phenomenon of the electric double-layer. In this embodiment, the electricity accumulating unit 111 is a comprehensive or inclusive unit including the so-called storage battery or storage cell and the so-called electricity accumulating device.

The electricity accumulating unit 111 may directly supply the accumulated electric power to the glucose sensor 4, or the electricity accumulating unit 111 may supply the electric power to the glucose sensor 4 via any other electronic part. In this embodiment, the electric power, which is fed from the electricity accumulating unit 111, is firstly supplied to the sensor control unit 12, and the electric power is supplied to the glucose sensor 4 via the sensor control unit 12. The power generating unit 110 generates the driving electric power to drive the glucose sensor 4. Further, the electric power supply device 11 may have an unillustrated primary battery for reserve or backup (for example, button battery or the like) as an emergency power source. In the ordinary situation, the glucose sensor 4 can be sufficiently driven by the electric power furnished by the electricity accumulating unit 111. Therefore, the electric power of the primary battery for reserve or backup is not consumed.

It is not necessarily indispensable that the electric power supply device 11 should be provided at the inside of the casing 2. The electric power supply device 11 can be also installed at the outside of the casing 2. Alternatively, the electric power supply device 11 may be accommodated at the inside of the casing 17 of the display unit component 14, or the electric power supply device 11 may be attached to the outer surface of the casing 17. Further alternatively, the power generating unit 110 and the electricity accumulating unit 111 can be also arranged separately respectively in the casing 2 on the side of the sensor control unit 12 and in the casing 17 on the side of the display unit component 14 respectively by the aid of a cable or the like.

As for the measuring apparatus 1, the continuous (successive) measurement (monitoring) period is preferably several days and more preferably about 1 week to several weeks. It is assumed that the glucose concentration is continuously measured every constant periods (for example, approximately at a frequency of once per several minutes) over a relatively long period of time. Therefore, it is preferable that the glucose concentration is automatically measured and the monitoring is continued as a matter of course even when an examinee is asleep in the night. The term "continuously" described above can be grasped to have the meaning of "intermittently".

In this arrangement, when only the primary battery is provided as the driving power source for the measuring apparatus 1, if the electric energy, which is accumulated in the primary battery, is consumed and exhausted during the continuous monitoring period, especially in the night when the examinee is asleep, then the supply of the driving electric power is stopped with respect to the glucose sensor 4 and other electronic parts. If such a situation arises, the monitoring of the glucose concentration is interrupted, which is extremely inconvenient. For example, the diabetes patient tends to be in hypoglycemia when the patient is asleep. If the monitoring is interrupted in such a circumstance, for example, the following situation arises. That is, it is impossible to give a warning that the glucose concentration indicates an abnormal value, by means of the warning apparatus. Further, it is impossible to regulate the insulin amount by making communication with the insulin injector.

In view of the above, the electric power supply device 11 according to this embodiment stores the electric power generated by the power generating unit 110 (performs the electricity accumulation) by means of the charging beforehand. If the power supply request for the glucose sensor 4 is given, the electric power, which is accumulated in the electricity accumulating unit 111, is supplied to the glucose sensor 4. In other words, the method for supplying the electric power to the glucose sensor 4 comprises a power generating step of generating the electric power for driving the glucose sensor 4, a charging step of performing charging (accumulation) with the electric power generated in the power generating step, and a supplying step of supplying the electric power accumulated in the charging step to the glucose sensor 4 if the power supply request for the glucose sensor 4 is given.

The power supply request is such a request that the driving electric power should be supplied to the glucose sensor 4. The power supply request is given at every timings at which the glucose concentration is measured by the glucose sensor 4. The measurement timings for measuring the glucose concentration are previously determined, for example, as constant intervals (for example, every several minutes). In addition thereto, the power supply request for the glucose sensor 4 is also given if a predetermined operation (for example, depression of a measurement start button) is performed by a user. The power supply request is given by the user, for example, at indefinite intervals (irregularly or in an unscheduled manner). The electric power is fed from the electricity accumulating unit 111 to the sensor control unit 12 by using the trigger of the power supply request for the glucose sensor 4, and the driving voltage is applied from the sensor control unit 12 to the glucose sensor 4. Examples will be described more specifically below.

Example 1

Figure 4:
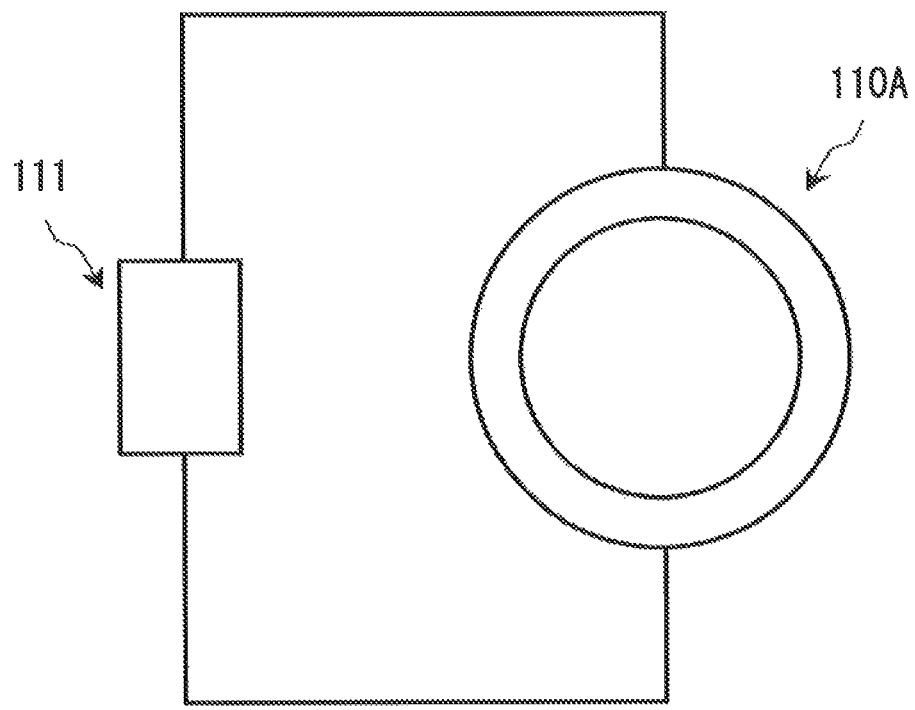
FIG. 4 illustrates a power generating unit in relation to Example 1.

FIG. 4 illustrates a power generating unit 110 in relation to Example 1. Example 1 has such a feature that the electric power for driving the glucose sensor 4 is generated by utilizing the piezoelectric effect which utilizes the pressure or the vibrational energy allowed to act in an environment of use.

The power generating unit 110 of Example 1 includes a piezoelectric element 110A which generates the electric power by performing the piezoelectric conversion. The piezoelectric element 110A can be constructed by a piezoelectric member which converts the acting vibration and/or the acting pressure into the electric power, and an electrode which is connected to the piezoelectric member. The piezoelectric element 110A may be provided in such a mode that the external force is allowed to act directly. Alternatively, as shown in FIG. 5, the piezoelectric element 110A may be provided in such a mode that the strain energy, which is brought about when the strain is caused by the acting vibrational energy, is converted into the electric power.

Figure 5:
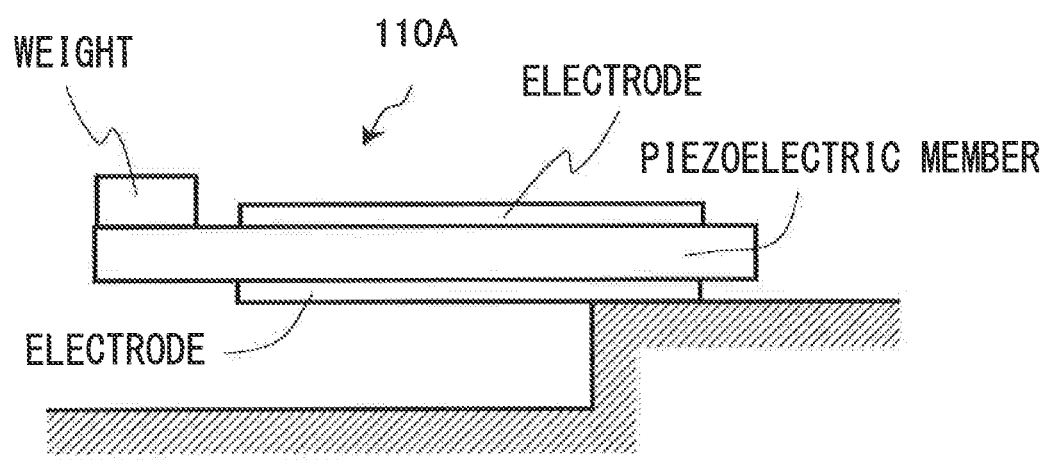
FIG. 5 illustrates a piezoelectric element in relation to Example 1.

In an example shown in FIG. 5, a piezoelectric member, which is interposed by electrodes, is supported in a form of cantilever. In FIG. 5, a weight is installed on the free end side of the piezoelectric member of the piezoelectric element 110A so that the piezoelectric element 110A is displaced with ease. In this arrangement, the piezoelectric element 110A is deformed (strained) when the vibrational energy is transmitted to the piezoelectric element 110A. As a result, the energy is converted into the electric power in accordance with the so-called piezoelectric effect.

In particular, the electric power supply apparatus 11 according to this embodiment is carried on the measuring apparatus 1 installed to an examinee. Accordingly, the vibration and the pressure, which are accompanied by various actions in the daily life of the examinee, can be appropriately allowed to act on the piezoelectric element 110A. That is, the driving electric power, which is to be supplied to the glucose sensor 4, is generated unconsciously while the examinee is not conscious of the action.

The electric power, which is generated by the power generating unit 110 as described above, is charged and accumulated in the electricity accumulating unit 111. Every time when the power supply request is given for the glucose sensor 4, the electric power, which is accumulated in the electricity accumulating unit 111, is supplied to the glucose sensor 4. Accordingly, it is possible to appropriately drive the glucose sensor 4. For example, when the glucose concentration is measured when the examinee is asleep, the electric power supply to the glucose sensor 4 is furnished with the electric power accumulated in the electricity accumulating unit 111. After the examinee gets up, the power generation is restarted by the power generating unit 110, and it is possible to increase the electricity accumulation amount in the electricity accumulating unit 111.

As described above, according to the electric power supply device 11 and the measuring apparatus 1 provided with the same, it is possible to continuously supply the driving electric power stably to the glucose sensor 4, even when the continuous monitoring period, in which the glucose concentration is measured continuously in succession by the measuring apparatus 1, continues for a long period of time. Therefore, it is possible to suppress such an inconvenience that the monitoring of the glucose concentration is interrupted during the continuous monitoring period. Therefore, even when the glucose concentration of the examinee indicates any abnormal value when the examinee is asleep, then the warning can be reliably given by the warning apparatus, and the insulin amount can be regulated to be a proper amount by means of the data communication with the insulin injector. Further, according to this arrangement, the power generation can be performed by utilizing the pressure or the vibrational energy allowed to act in an environment of use, and the glucose sensor 4 can be driven by using the electric power. Therefore, this arrangement is effective in view of the cost as well. Therefore, it is possible to mitigate the economic load of the examinee as compared with when the driving electric power of the glucose sensor 4 counts on only the primary battery.

Example 2

Figure 6:
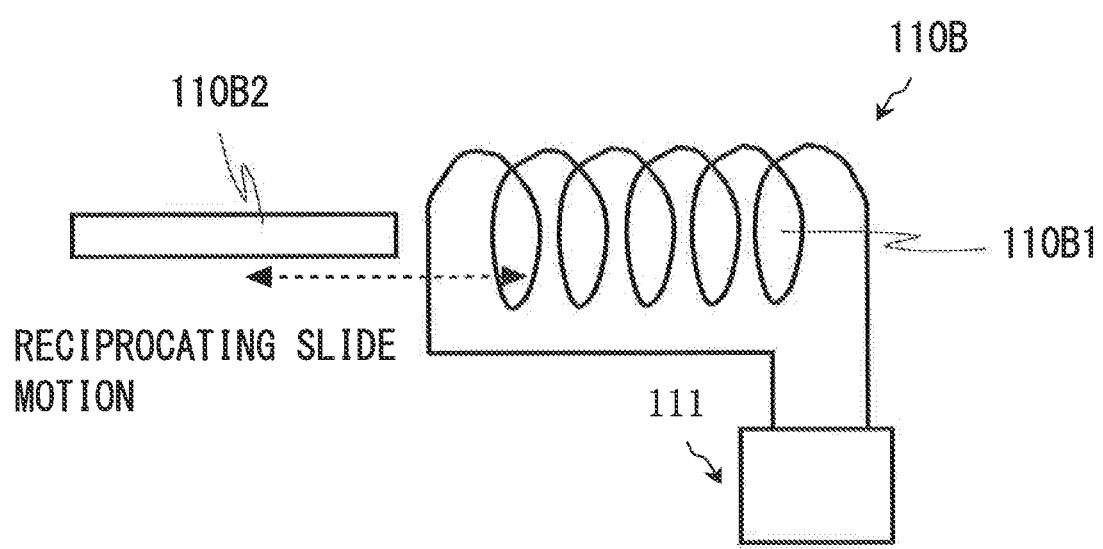
FIG. 6 illustrates a power generating unit in relation to Example 2.

FIG. 6 illustrates a power generating unit 110 in relation to Example 2. Example 2 has such a feature that the electric power for driving the glucose sensor 4 is generated by utilizing the action of the electromagnetic induction which utilizes the vibrational energy allowed to act in an environment of use.

In Example 2, the power generating unit 110 is constructed to include a generator (hereinafter referred to as "electromagnetic induction generator") 110B which generates the electric power in accordance with the action of the electromagnetic induction which utilizes the vibrational energy allowed to act in an environment of use. As shown in the drawing, the electromagnetic induction generator 110B has an electromagnetic induction coil 110B1 and a permanent magnet 110B2. The electromagnetic induction coil 110B1 and the permanent magnet 110B2 are provided respectively such that the relative positional relationship therebetween is changed by means of the vibrational energy as the driving force so that the magnetic flux (magnetic field) is changed in the electromagnetic induction coil 110B1.

Various known mechanisms can be adopted as a specified mechanism for holding the electromagnetic induction coil 110B1 and the permanent magnet 110B2. For example, it is also allowable to adopt a slide mechanism in which the permanent magnet 110B2 is subjected to the reciprocating slide motion in the axial direction of the electromagnetic induction coil 110B1. The magnetic flux of the electromagnetic induction coil 110B1 may be changed to generate the induced electromotive force by repeating the insertion and the extraction of the permanent magnet 110B2 with respect to the electromagnetic induction coil 110B1 by utilizing the vibrational energy allowed to act in an environment of use.

As described above, according to the electromagnetic induction generator 110B, the driving electric power, which is to be supplied to the glucose sensor 4, can be generated unconsciously while the examinee is not conscious of the action, in the same manner as the piezoelectric element 110A of Example 1. That is, the driving electric power for the glucose sensor 4 can be appropriately accumulated in the electricity accumulating unit 111 by utilizing various actions in the daily life of the examinee. Therefore, it is possible to continuously supply the driving electric power stably to the glucose sensor 4, even when the continuous monitoring period, in which the glucose concentration is measured continuously, continues for a long period of time. It is possible to appropriately avoid such a situation that the monitoring of the glucose concentration is interrupted against examinee's will.

Example 3

Figure 7:
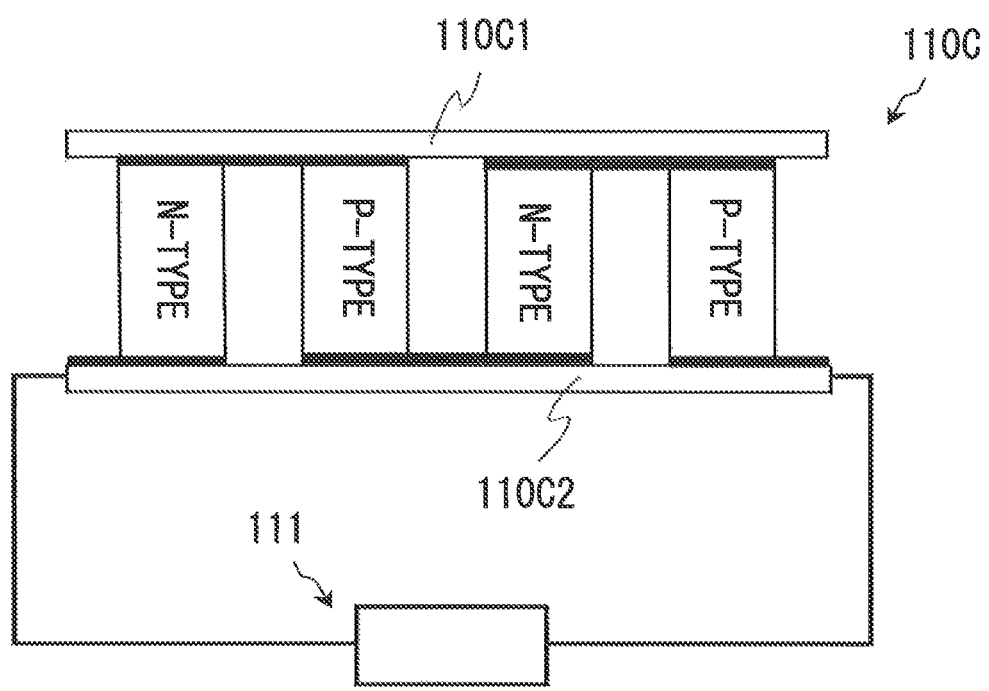
FIG. 7 illustrates a power generating unit in relation to Example 3.

FIG. 7 illustrates a power generating unit 110 in relation to Example 3. Example 3 has such a feature that the electric power for driving the glucose sensor 4 is generated by utilizing the thermoelectric effect which utilizes the temperature difference between the body temperature of an examinee and the environmental temperature in an environment of use.

In Example 3, the power generating unit 110 is constructed to include a Seebeck element 110C which generates the electric power by performing the thermoelectric conversion by utilizing the temperature difference between the body temperature of an examinee and the environmental temperature in an environment of use. As shown in the drawing, the Seebeck element 110C is a thermoelectric conversion element for performing the power generation by utilizing the Seebeck effect in which the electromotive force is generated when N-type and P-type semiconductors are subjected to the PN junction and the temperature difference is provided between the both ends thereof. A first terminal 110C1 is provided on one end side of the junction portion of the Seebeck element 110C, and a second terminal 110C2 is provided on the other end side.

The Seebeck element 110C is provided, for example, in such a mode that the body temperature of the examinee is transmitted to the first terminal 110C1, and the external environmental temperature is transmitted to the second terminal 110C2. Accordingly, the temperature difference is provided between the first terminal 110C1 and the second terminal 110C2, for example, by utilizing the temperature difference between the ambient temperature and the body temperature of the examinee, and the electric power can be generated by utilizing the Seebeck effect resulting from the temperature difference. Further, the electric power can be generated by utilizing the temperature difference between the body temperature and the temperature of water fed, for example, during bathing. Specifically, for example, the first terminal 110C1 is provided in such a mode that the first terminal 110C1 is exposed to the external environment, for example, via a protective film which is excellent in the waterproof performance and the thermal conductivity. As a result, for example, the temperature of the external environment (ambient temperature, water temperature brought about, for example, during bathing) is introduced into the first terminal 110C1. On the other hand, the second terminal 110C2 is provided in such a mode that the second terminal 110C2 is shut off from the outside and the second terminal 110C2 makes tight contact with the skin, for example, via a protective film which is excellent in the waterproof performance and the thermal conductivity as well. Accordingly, the body temperature is introduced into the second terminal 110C2. Accordingly, the temperature difference between the body temperature and the external environment, which is spontaneously generated in the daily life of the examinee, is brought about between the first terminal 110C1 and the second terminal 110C2. As a result, the electric power is generated by the Seebeck element 110C.

As described above, according to the Seebeck element 110C of Example 3, the driving electric power, which is to be supplied to the glucose sensor 4, can be generated unconsciously while the examinee is not conscious of the action, in the same manner as in Example 1 and Example 2. That is, the driving electric power for the glucose sensor 4 can be appropriately accumulated in the electricity accumulating unit 111 by utilizing various actions in the daily life of the examinee.

Example 4

Figure 8:
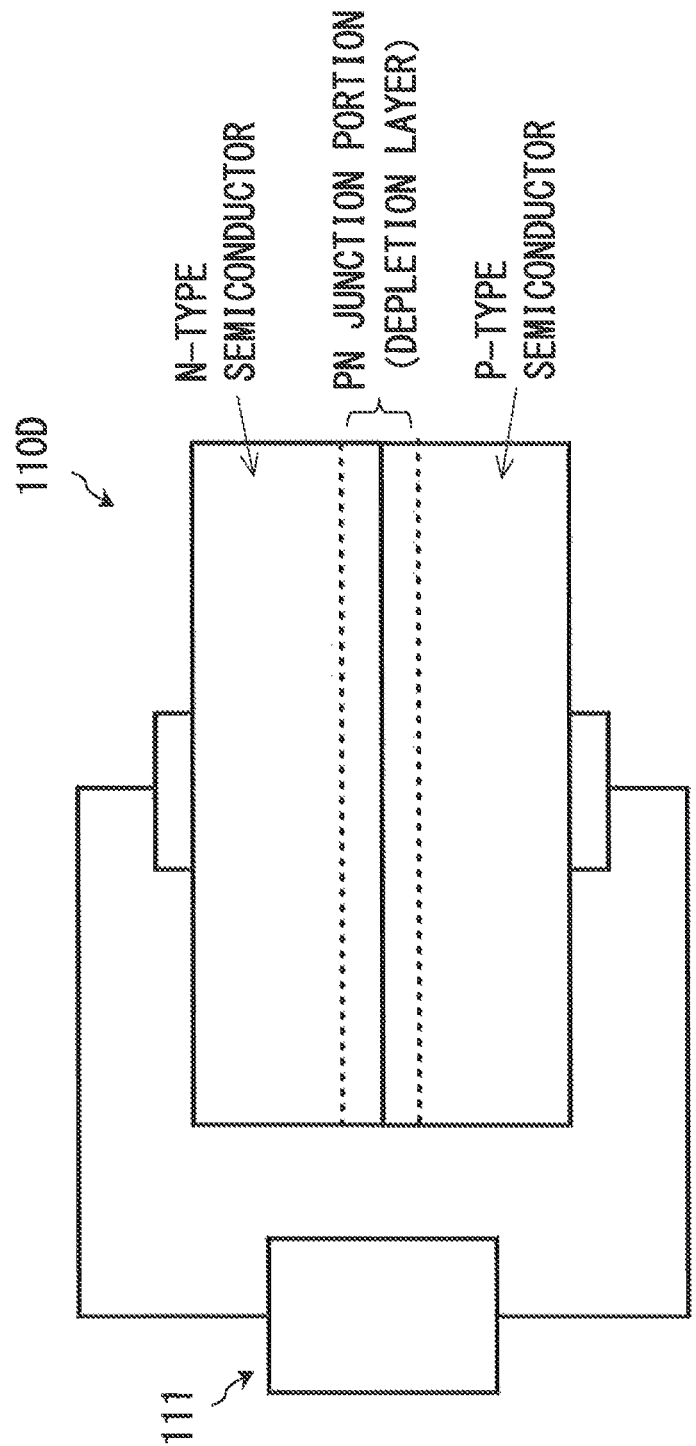
FIG. 8 illustrates a power generating unit in relation to Example 4.

FIG. 8 illustrates a power generating unit 110 in relation to Example 4. Example 4 has such a feature that the electric power is generated to drive the glucose sensor 4 by utilizing the photoelectric effect which utilizes the light energy received in an environment of use.

In Example 4, the power generating unit 110 is constructed to include a solar cell 110D which generates the electric power by performing the photoelectric conversion by utilizing the light energy received in an environment of use. The solar cell 110D is an electric power device which directly converts the light energy into the electric power by utilizing the photoelectromotive force effect. The solar cell 110D shown in FIG. 8 conceptually represents a so-called silicon solar cell. The solar cell 110D has such a structure that N-type and P-type semiconductors are subjected to the PN junction. Valence electrons of the semiconductor are excited by allowing the light energy to act on the PN junction portion. The photoelectromotive force effect, in which the positive holes at the PN junction portion are attracted toward the P-type semiconductor and the electrons are attracted toward the N-type semiconductor, is caused, and the photoelectromotive force is produced thereby. The solar cell 110D of this embodiment is not limited to the silicon solar cell. It is also possible to preferably adopt other types of solar cells including, for example, a dye-sensitized solar cell.

According to this arrangement, the photoelectric conversion can be performed to generate the electric power by utilizing various types of the light energy received by the examinee in the daily life, including, for example, the sunlight received in the daytime and the illumination light received from an illumination apparatus. Therefore, the driving electric power for the glucose sensor 4 can be generated by the solar cell 110D as well, while the examinee is unconscious of the action, in the same manner as in other Examples.

Example 5

Figure 9:
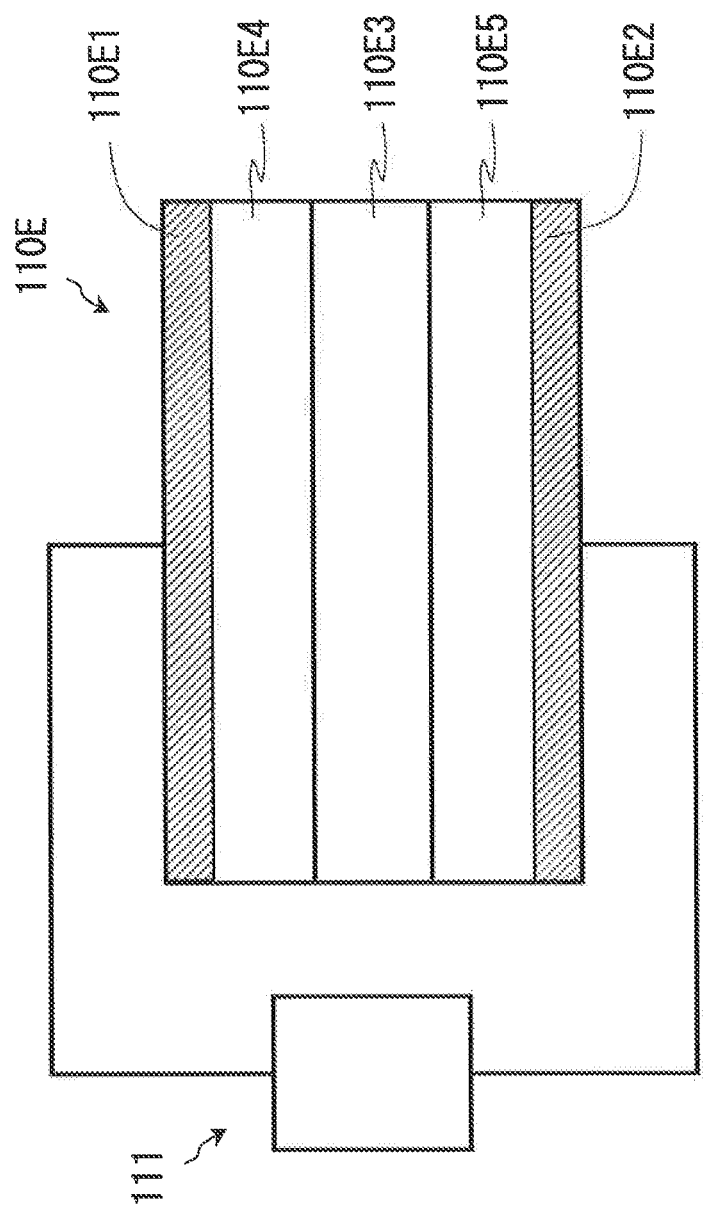
FIG. 9 illustrates a power generating unit in relation to Example 5.

FIG. 9 illustrates a power generating unit 110 in relation to Example 5. In Example 5, the power generating unit 110 has a fuel cell 110E, and the electric power is generated by using the fuel cell 110E. The fuel cell 110E is a generator which takes out the electric power by means of the electrochemical reaction. In the fuel cell 110E of Example 5, the fuel is decomposed by enzyme to make separation into protons and electrons. The fuel cell 110E is a biofuel cell which can appropriately use, as fuel, biofuel including, for example, alcohols such as methanol and ethanol and sugars, for example, such as glucose.

As shown in FIG. 9, the fuel cell 110E has an electrolyte film 110E3 which allows proton to conduct, and an anode layer 110E4 and a cathode layer 110E5 which are joined to both surfaces thereof. An anode (negative electrode, fuel electrode) 110E1 is joined to the anode layer 110E4, and a cathode (positive electrode, oxidant electrode) 110E2 is joined to the cathode layer 110E5. A solution of sugar, which serves as fuel, is supplied to the side of the anode 110E1, and oxygen or air is supplied to the side of the cathode 110E2. On the side of the cathode 110E2, hydroxide ion ($OH^-$) is produced in accordance with the reduction of oxygen, which is moved in the film or membrane to arrive at the side of the anode 110E1. On the side of the anode 110E1, sugar and $OH^-$ are reacted to produce oxide of sugar and water. During this process, electrons flow through an external circuit, and it is possible to take out the current. The fuel cell 110E further comprises a fuel tank which stores the fuel to be supplied to the anode 110E. For example, an insulating material such as acrylic resin or the like is used for the fuel tank.

According to the arrangement as described above, the electric power can be conveniently generated by the fuel cell 110E by using the fuel which exists on the examinee's side in the daily life of the examinee, for example, the fuel of sugars contained in drinks and alcohols including, for example, juices, sports drinks, sugared water, and alcohols. That is, it is possible to accept such a merit that any arbitrary fuel can be supplemented at any arbitrary place. The electric power, which is generated by the fuel cell 110E as described above, is accumulated in the electricity accumulating unit 111 by being charged. When the power supply request is given for the glucose sensor 4, the electric power, which is accumulated in the electricity accumulating unit 111, is supplied to the glucose sensor 4. Therefore, even when the continuous monitoring period of the measuring apparatus 1 continues for a long period of time, the driving electric power can be continuously supplied stably to the glucose sensor 4. In the fuel cell 110E in this embodiment, any fuel for reserve can be provided as a cartridge for the purpose of backup.

As described above, Examples have been explained as Examples 1 to 5 in relation to the electric power supply device 11. However, the power generating units 110, which are explained in respective Examples, can be used or carried out while being combined with each other as far as possible.

The measuring apparatus 1 of this embodiment quantitatively measures the test substance by measuring the glucose concentration in the body fluid. However, it is also possible to apply the present invention in order to quantitatively evaluate the test substance, for example, when the judgment is made about whether or not test substance exists in a certain area around the sensor unit of the electrochemical sensor or about whether or not the test substance exceeds a certain level.

In this embodiment, the casing 2 (also referred to as "main body portion" in this section), in which the control computer 3 of the measuring apparatus 1 is accommodated, is fixed on the skin of the examinee. However, the casing 2 may be attached, for example, to the clothing of the examinee, or the casing 2 may be accompanied by means of any other method. However, it is not necessarily indispensable that the main body portion of the measuring apparatus 1 should be attached to the examinee. For example, the following procedure is also available. That is, the electric signal, which is generated by the glucose sensor 4, is transmitted in a wireless manner to the control computer 3 installed at a place separated from the examinee. The glucose concentration is calculated by the sensor control unit 12 which is realized in the control computer 3.

The test substance in the body fluid is not limited to glucose, which may be, for example, lactic acid. In this case, the electrochemical sensor functions as a lactic acid sensor for measuring the level of lactic acid. For example, lactate oxidase may be immobilized to the sensor unit (immobilized enzyme unit) thereof. Further, for example, bile acid can be exemplified as another preferred test substance. However, as for the test substance, the present invention can be appropriately carried out by using any specified substance contained in any sample other than the body fluid as the test substance. Other than the enzyme, it is possible to appropriately apply, for example, microorganisms, antibodies, and cells as the biological material held by the sensor unit of the electrochemical sensor.

In this embodiment, the electrochemical sensor, which generates the electric signal, is adopted as the sensor according to the present invention. However, for example, it is also possible to adopt a sensor which generates a signal correlated with the amount or the concentration of a test substance contained in a sample by continuously detecting the reflected light. This embodiment is illustrative of the exemplary case in which the present invention is applied when the numerical information in relation to the test substance in the body fluid of human (examinee) is measured. However, it is of course allowable that a body fluid of any other objective (for example, any animal other than human) is used as a sample. These matters are also applicable equivalently to other embodiments explained below.

Second Embodiment

Figure 10:
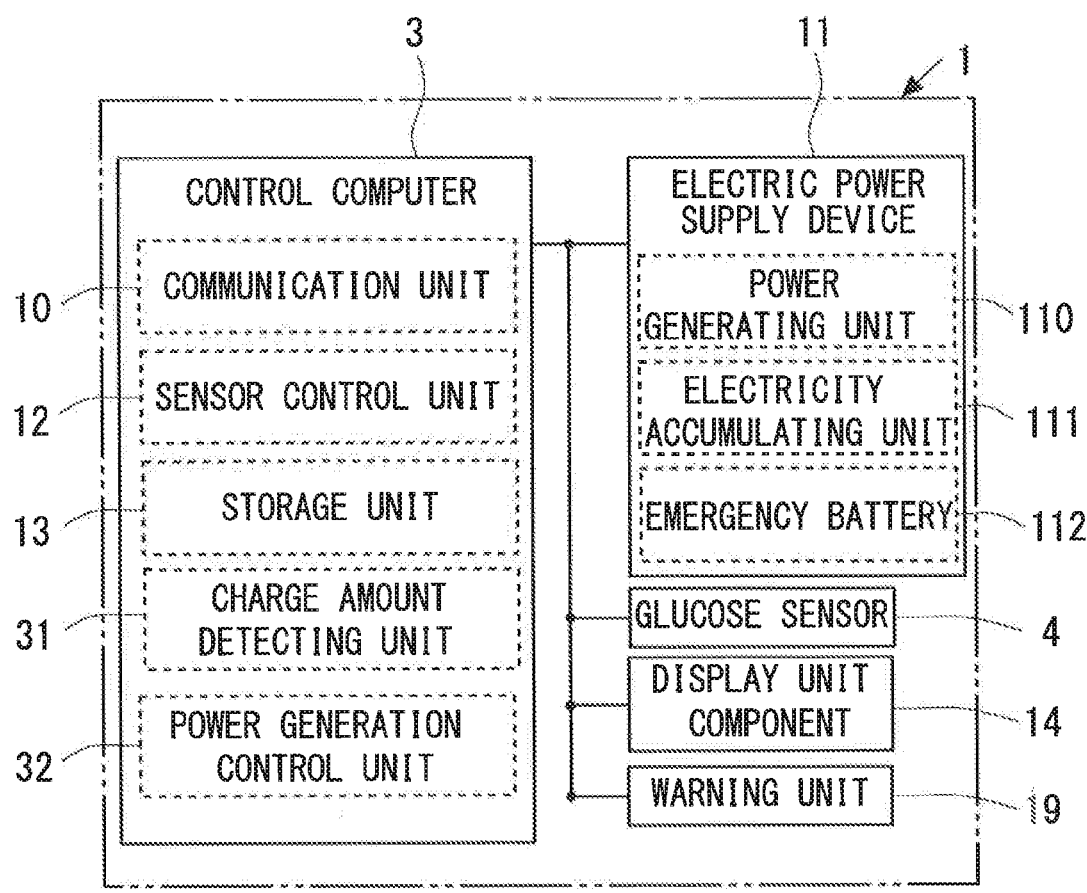
FIG. 10 shows a block diagram illustrating main components of a measuring apparatus according to a second embodiment.

Next, a second embodiment for carrying out the present invention will be explained. In this embodiment, the components or parts, which are common to those of the first embodiment, are designated by the same reference numeral, any detailed explanation of which is omitted thereby. The glucose sensor 4 in the second embodiment is the same as or equivalent to that of the first embodiment. FIG. 10 shows a block diagram illustrating main components of a measuring apparatus 1 according to the second embodiment. An explanation will now be made principally about the difference from the first embodiment. In this embodiment, the control computer 3 of the measuring apparatus 1 further includes a charge amount detecting unit 31 and a power generation control unit 32. These are functions realized by executing various control programs by the processor of the control computer 3. The measuring apparatus 1 includes a warning unit 19 which outputs a warning sound and voice information. Further, the electric power supply device 11 includes a primary battery for reserve or backup (hereinafter referred to as "emergency battery") 112 as an emergency power source. The emergency battery 112 is, for example, a button battery. However, there is no limitation thereto. In this embodiment, the emergency battery 112 corresponds to the emergency power source according to the present invention. The other basic components or parts of the measuring apparatus 1 according to this embodiment are the same as or equivalent to those of the first embodiment.

The power generating unit 110, which is carried on the measuring apparatus 1 concerning each of Examples (see each of Examples in the first embodiment), has such a merit that the driving electric power, which is to be supplied to the glucose sensor 4, can be generated unconsciously when an examinee lives a daily life. However, if a state, in which the power generation amount of the power generating unit 110 is excessively small, continues, it is feared that the charging in the electricity accumulating unit 111 may be performed in a small amount and the measuring operation performed by the glucose sensor 4 may be inhibited. In view of the above, not only the charge amount (amount of charge) of the electricity accumulating unit 111 but also the power generation amount of the power generating device for constructing the power generating unit 110 is grasped after the start of the measurement in the measuring apparatus 1, and an appropriate process or treatment is performed depending on an obtained result. In this embodiment, the method for supplying the electric power to the glucose sensor 4 comprises a power generating step of generating an electric power for driving the glucose sensor 4, a monitoring step of monitoring a power generation amount generated in the power generating step, a charging step of performing charging (accumulation) with the electric power generated in the power generating step, and a supplying step of supplying the electric power accumulated in the charging step to the glucose sensor 4.

The charge amount detecting unit 31 of the control computer 3 is a voltage detection circuit for detecting the voltage of the electricity accumulating unit 111. The voltage value of the electricity accumulating unit 111 is detected, and the charge amount thereof is detected thereby. In other words, the charge amount detecting unit 31 detects the voltage value of the electric power supplied from the electricity accumulating unit 111 to the glucose sensor 4. Further, the power generation control unit 32 of the control computer 3 monitors the power generation amount generated by the power generating unit 110 by detecting the electric power supplied from the power generating unit 110 to the electricity accumulating unit 111. Further, the power generation control unit 32 calculates the power generation rate Rg defined as the power generation amount per unit time in the power generating unit 110, when the power generation amount generated by the power generating unit 110 is monitored. The power generation situation of the power generating unit 110 is controlled depending on the magnitude of the power generation rate Rg of the electric power generated by the power generating unit 110. The warning unit 19 outputs predetermined warning information if the power generation rate Rg of the electric power generated by the power generating unit 110 is low. The power generation rate Rg calculated in this step is successively stored in the storage unit 13 of the control computer 3.

Figure 11:
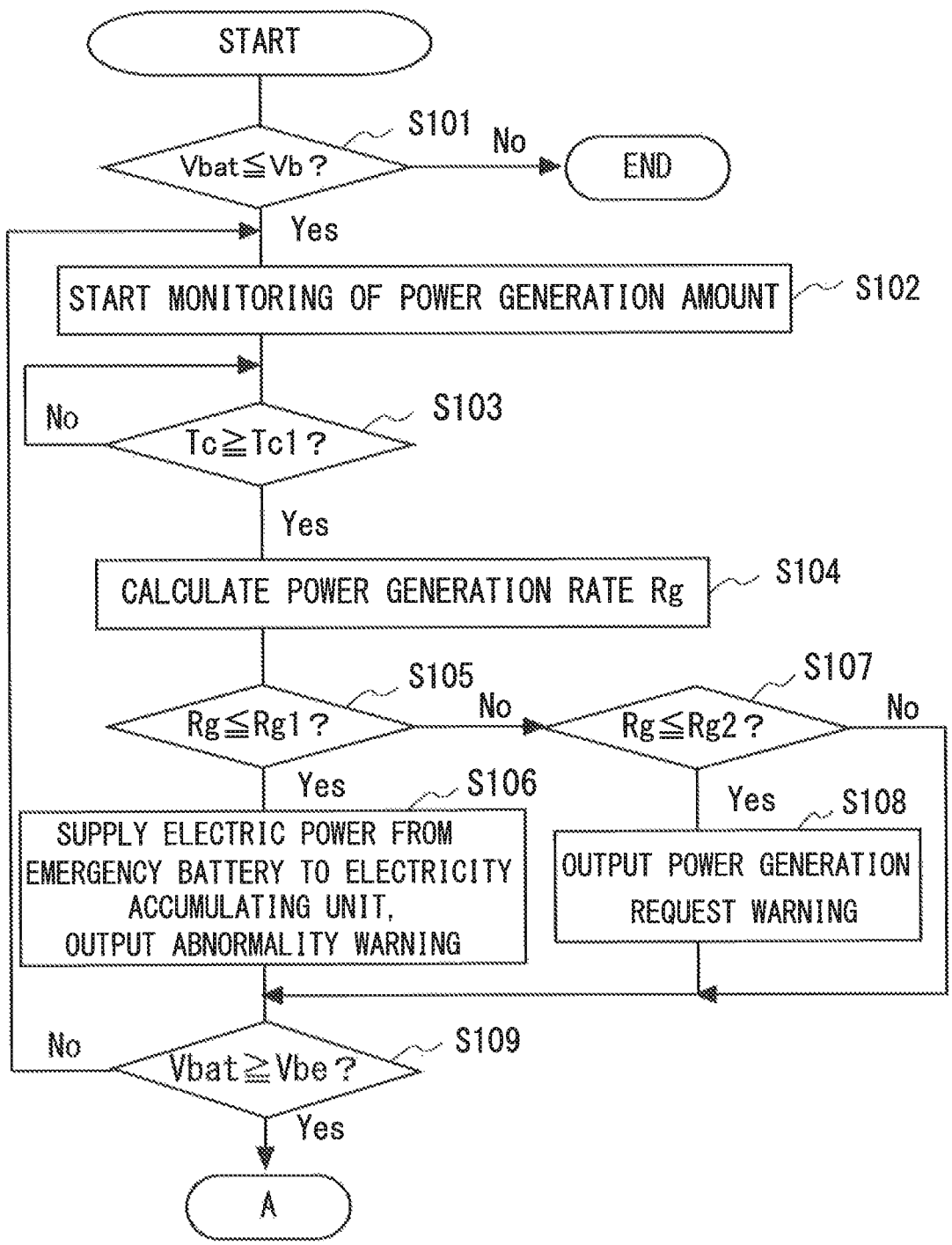
FIG. 11 shows a flow chart illustrating the process contents of a first half portion of a control routine in the second embodiment.
Figure 12:
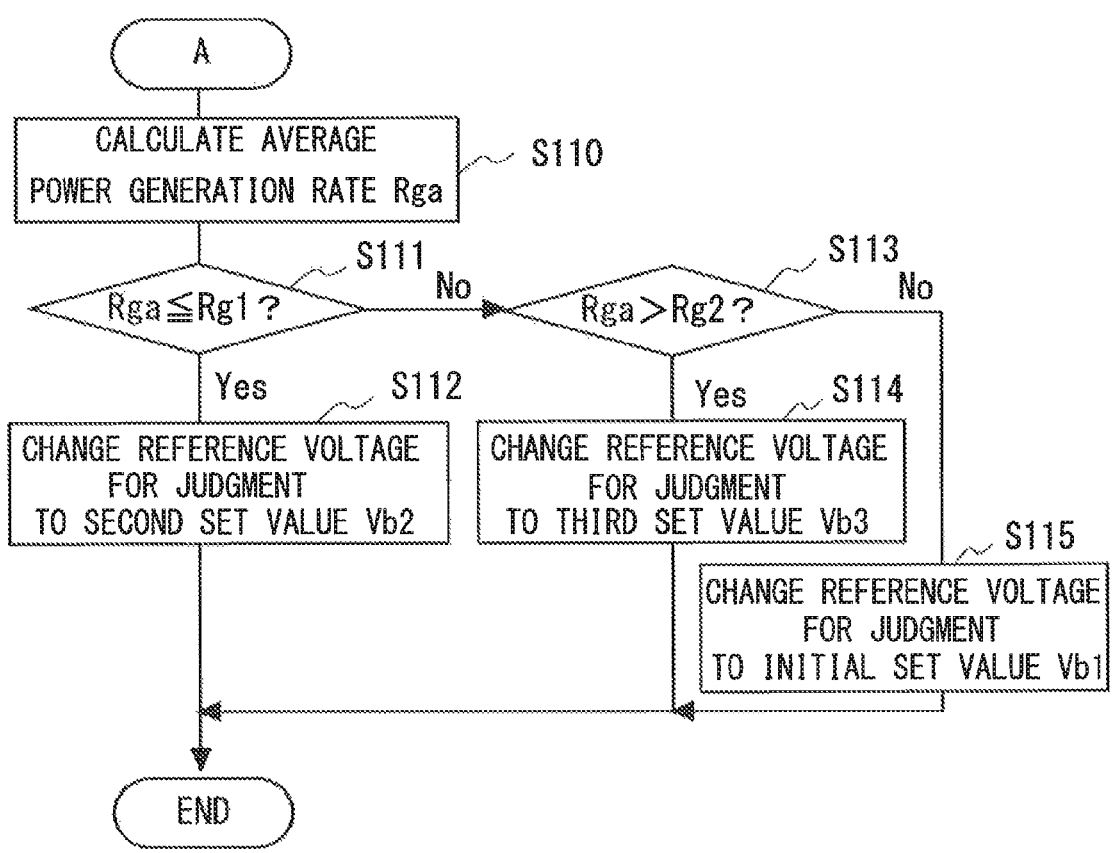
FIG. 12 shows a flow chart illustrating the process contents of a latter half portion of the control routine in the second embodiment.

FIGS. 11 and 12 show flow charts illustrating a control routine in the second embodiment. FIG. 11 shows the process contents of the first half portion of this control routine, and FIG. 12 shows the process contents of the latter half portion. In this procedure, the measuring apparatus 1 performs the monitoring (observation) for the power generation amount in the power generating unit 110. If the power generation amount is low, then the warning information is outputted to the outside acoustically and/or visually, and/or the electric power is supplied from the emergency battery 112 to the glucose sensor 4.

In this control routine, the respective processes shown in the drawings are realized by developing the control programs stored in ROM to RAM by the control computer 3 and executing the control programs by the processor. This control routine is repeatedly executed every certain periods of time by the control computer 3 in a state in which the power source of the measuring apparatus 1 is turned ON.

When this control routine is started, then the control computer 3 (charge amount detecting unit 31) detects the voltage (hereinafter referred to as "charging voltage") Vbat of the electricity accumulating unit 111 in Step S101, and the magnitude correlation is judged with respect to a reference voltage for judgment Vb. The reference voltage for judgment Vb is a threshold value to judge whether or not the monitoring of the power generation amount generated by the power generating unit 110 is to be started. The initial set value of the reference voltage for judgment Vb is set to a value Vb1 incorporated with a predetermined margin with respect to a voltage value minimally required to perform the measurement of the blood sugar level (glucose concentration) without causing any trouble. The initial set value Vb1 of the reference voltage for judgment Vb is stored in a nonvolatile area of the storage unit 13. The storage contents can be retained even when the power source of the measuring apparatus 1 is turned OFF.

If the affirmative judgment is made in Step S101 (Vbat≤Vb), the routine proceeds to Step S102. If the affirmative judgment is not made (Vbat>Vb), this routine is once completed. In Step S102, the power generation control unit 32 starts the power generation amount monitoring process for monitoring the power generation amount generated by the power generating unit 110. In the power generation amount monitoring process, the power generation control unit 32 periodically acquires the voltage Vbat of the electricity accumulating unit 111 detected by the charge amount detecting unit 31. It is possible to obtain the electric power fed from the power generating unit 110 to the electricity accumulating unit 111, i.e., the power generation amount brought about by the power generating unit 110, on the basis of the acquired value.

The control computer 3 measures the power generation amount monitoring period Tc as the elapsed period from the start of the power generation amount monitoring process, by using a timer. In Step S103, the control computer 3 judges whether or not the power generation amount monitoring period Tc is not less than a reference period Tc1. If the power generation amount monitoring period Tc is less than the reference period Tc1, the judgment in Step S103 is performed again after a certain period. If it is judged in Step S103 that the power generation amount monitoring period Tc is not less than the reference period Tc1, the routine proceeds to Step S104. In Step S104, the control computer 3 (power generation control unit 32) calculates the power generation rate Rg as the power generation amount generated by the power generating unit 110 per unit time in the power generation amount monitoring period Tc.

In Step S105, the control computer 3 (power generation control unit 32) judges whether or not the calculated power generation rate Rg is not more than a first reference power generation rate Rg1. If the affirmative judgment is made in Step S105 (Rg≤Rg1), the routine proceeds to Step S106. On the other hand, if the negative judgment is made in Step S105 (Rg>Rg1), then the routine proceeds to Step S107, and the control computer 3 (power generation control unit 32) judges whether or not the power generation rate Rg is not more than a second reference power generation rate Rg2. If the affirmative judgment is made in Step S107 (Rg≤Rg2), the routine proceeds to Step S108. If the affirmative judgment is not made in Step S107 (Rg>Rg2), the routine proceeds to Step S109 as it is.

In Step S106, the control computer 3 allows the emergency battery 112 of the electric power supply device 11 to supply the electric power therefrom to the electricity accumulating unit 111. In this procedure, the first reference power generation rate Rg1 is such a threshold value of the power generation rate that it is judged that any trouble arises in the measurement of the glucose concentration (blood sugar level) by the measuring apparatus 1 if the state, in which the power generation rate Rg in the power generating unit 110 is not more than the first reference power generation rate Rg1, is continued. It is appropriate that a proper value is previously determined for the first reference power generation rate Rg1 on the basis of any rule of thumb such as an experiment or the like. Further, in this step, the control computer 3 allows the warning unit 19 to output an abnormality warning. The abnormality warning is acoustical or visual warning information in order to inform those around an examinee (patient) of such a possibility that the examinee (patient) may be inactive due to any trouble or sleeping, for example, such a possibility that the examinee (patient) may fall into a comatose state due to hypoglycemia. It is more preferable that a warning is given by voice so that people around the examinee, who are separated from the examinee, can be informed of the abnormality of the examinee. If the process of this step is completed, the routine proceeds to Step S109. The process contents of Step S109 will be described later on. If the electric power supply is already started from the emergency battery 112 (emergency power source) to the electricity accumulating unit 111 at the point in time at which the routine proceeds to Step S106, it is appropriate that the routine proceeds to Step S109 while maintaining the state.

The second reference power generation rate Rg2 is such a threshold value of the power generation rate that it is possible to judge that the power generation amount is sufficiently secured in the power generating unit 110 if the power generation rate Rg exceeds the value of the second reference power generation rate Rg2. The second reference power generation rate Rg2 is set as the value which is larger than that of the first reference power generation rate Rg1. If the power generation rate Rg is higher than the first reference power generation rate Rg1 and not more than the second reference power generation rate Rg2, the power generation amount is secured to some extent although it is not affirmed that the power generation amount is sufficient in the power generating unit 110. Therefore, the possibility of occurrence of any abnormality such as a comatose state or the like in an examinee (patient) is low. In such a situation, it is contemplated to increase the power generation amount in the power generating unit 110 by hastening the examinee to perform the power generating action. Specifically, in Step S107, the control computer 3 allows the warning unit 19 to output a power generation request warning. The power generation request warning is acoustical or visual information to hasten the examinee (patient) to perform the power generating action.

The power generating unit 110 of the electric power supply device 11 is constructed by any one of the power generating devices explained in Examples 1 to 5 in the first embodiment or by combining a plurality of them. When the power generating unit 110 includes the piezoelectric element 110A (see Example 1) which generates the electric power in accordance with the piezoelectric effect by utilizing the pressure or the vibrational energy allowed to act in an environment of use, or the electromagnetic induction generator 110B (see Example 2) which generates the electric power in accordance with the electromagnetic induction by utilizing the vibrational energy, it is appropriate to output the power generation request warning of the contents to hasten the examinee (patient) to actively move the body, for example, to perform the exercise.

When the power generating unit 110 includes the Seebeck element 110C (see Example 3) which generates the electric power in accordance with the thermoelectric effect by utilizing the temperature difference between the body temperature of the examinee and the environmental temperature in an environment of use, it is appropriate to output the power generation request warning of the contents to hasten the examinee (patient) to take a bath or hasten the examinee (patient) to move to a place at which the temperature difference is large between the body temperature and the temperature (for example, a cold place or a hot place) so that the temperature difference is increased between the external environmental temperature and the body temperature of the examinee as described above.

When the power generating unit 110 includes the solar cell 110D (see Example 4) which generates the electric power in accordance with the photoelectric effect by utilizing the light energy received in an environment of use, it is appropriate to output the power generation request warning of the contents to hasten the examinee (patient) to move to a place at which the light can be received as much as possible. When the power generating unit 110 includes the fuel cell 110E (see Example 5), it is appropriate to output the power generation request warning of the contents to hasten the examinee (patient) to supply sugar or alcohol as the fuel to the fuel cell 110E. If the process of Step S108 is completed, the routine proceeds to Step S109.

On the other hand, if it is judged in Step S107 that the power generation rate Rg is higher than the second reference power generation rate Rg2, it is judged that the power generation amount produced by the power generating unit 110 is sufficiently secured. It is also considered that the output of the warning to hasten the examinee to perform the power generating action, which is given in the situation as described above, is troublesome for the examinee. Therefore, in such a case, the routine proceeds to Step S109 as it is.

In Step S109, the control computer 3 (charge amount detecting unit 31) detects the charging voltage Vbat in the electricity accumulating unit 111, and it is judged whether or not the charging voltage Vbat is not less than a charge completion reference voltage Vbe. The charge completion reference voltage Vbe is the voltage which serves as a reference to judge whether or not the charge amount is sufficient in the electricity accumulating unit 111 and whether or not the power generation amount monitoring process is to be completed. The charge completion reference voltage Vbe is previously set to an appropriate value on the basis of, for example, any rule of thumb. In this embodiment, the charge completion reference voltage Vbe is set to be higher than the reference voltage for judgment Vb.

If it is judged in Step S109 that the charging voltage Vbat is lower than the charge completion reference voltage Vbe (Vbat<Vbe), the routine returns to Step S102 after the count of the power generation amount monitoring period Tc is reset. In this case, the power generation amount monitoring process is continuously performed.

On the other hand, if it is judged in Step S109 that the charging voltage Vbat is not less than the charge completion reference voltage Vbe (Vbat≥Vbe), the routine proceeds to Step S110. In this control routine, the processes, which range from Step S101 to Step S109 described above, are designated as the power generation amount monitoring process, and the processes, which are performed in and after Step S110, are referred to as the monitoring start condition regulating process.

In Step S110, the control computer 3 (power generation control unit 32) calculates the average power generation rate Rga from the past power generation rates Rg stored in the storage unit 13. The average power generation rate Rga is obtained by averaging the values of the power generation rates measured in the past a plurality of times including the value stored most recently, of the power generation rates Rg stored in the storage unit 13. It is possible to appropriately change the number of pieces of data of the power generation rate Rg to be used in order to calculate the average power generation rate Rga.

In this control, according to the average power generation rate Rga calculated in Step S110, it is possible to grasp and judge an approximate tendency about the power generating action amount to generate the electric power in the power generating unit 110 in the living pattern (life habit or life style) of the examinee, especially the degree of the magnitude of the power generation amount per unit time. That is, if the average power generation rate Rga is high, it is possible to judge that the examinee (user) lives in accordance with a living pattern in which the power generating action is in a relatively large amount. On the contrary, if the average power generation rate Rga is low, it is possible to judge that the examinee lives in accordance with a living pattern in which the power generating action is in a relatively small amount. Accordingly, in this embodiment, the monitoring start condition regulating process is performed, wherein the value of the reference voltage for judgment, which serves as the threshold value to start the monitoring of the power generation amount in the power generating unit 110, is regulated depending on the average power generation rate Rga. If the process of Step S110 is completed, the routine proceeds to Step S111.

In S111, the control computer 3 (power generation control unit 32) judges whether or not the average power generation rate Rga is not more than the first reference power generation rate Rg1. If it is judged in Step S110 that the average power generation rate Rga is not more than the first reference power generation rate Rg1 (Rga≤Rg1), it is possible to judge that the examinee (user) lives in accordance with a living pattern in which the power generation amount per unit time is in a small amount (for example, a living pattern in which the body is scarcely moved actively). In this case, the routine proceeds to Step S112 to perform the process in which the frequency to perform the power generation amount monitoring process is raised by raising the reference voltage for judgment Vb to a value higher than the initial set value Vb1.

That is, in Step S112, the control computer 3 (power generation control unit 32) changes the value of the reference voltage for judgment Vb to a second set value Vb2 which is higher than the initial set value Vb1. For example, in this routine, the first reference power generation rate Rg1 is multiplied by a coefficient C1 (provided that C1>0 is given) to obtain a correction value Vb2 (Vb2>0) which is added to the initial set value Vb1 to calculate the second set value Vb2 thereby (Vb2=Vb1+ΔVb2, ΔVb2=C1×Rg1). The second set value Vb2, which is calculated as described above, is stored as the latest set value for the reference voltage for judgment Vb in a volatile area of the storage unit 13. That is, the set value of the reference voltage for judgment Vb in the storage unit 13 is updated to the second set value Vb2.

As a result, when this control routine is executed next time, the second set value Vb2, which is the latest reference voltage for judgment Vb stored in the storage unit 13, is adopted in the judging process in Step S101. Accordingly, the power generation amount monitoring process is started even when the charge amount in the electricity accumulating unit 111 is in a state of higher level with respect to the initial state. Therefore, the frequency to perform the power generation amount monitoring process is increased, and it is possible to give a larger number of opportunities to generate the electric power in the power generating unit 110. In Step S112, if the latest value of the reference voltage for judgment Vb stored in the storage unit 13 is the second set value Vb2, it is unnecessary to dare to update the value of the reference voltage for judgment Vb. If the process of this step is completed, this routine is completed.

On the other hand, if it is judged in Step S111 that the average power generation rate Rga is larger than the first reference power generation rate Rg1 (Rga>Rg1), the routine proceeds to Step S113. In Step S113, it is judged whether or not the average power generation rate Rga is larger than the second reference power generation rate Rg2. If it is judged that the average power generation rate Rga is larger than the second reference power generation rate Rg2 (Rga>Rg2), it is possible to judge that the examinee (user) lives in accordance with a living pattern in which the power generation amount per unit time is in a large amount (for example, a living pattern in which the body is frequently moved actively in many situations). In this case, the routine proceeds to Step S114 to perform the process in which the frequency to perform the power generation amount monitoring process is decreased by lowering the reference voltage for judgment Vb to a value lower than the initial set value Vb1.

That is, in Step S114, the control computer 3 (power generation control unit 32) changes the value of the reference voltage for judgment Vb to a third set value Vb3 which is lower than the initial set value Vb1. For example, in this routine, the second reference power generation rate Rg2 is multiplied by a coefficient C2 (provided that C2>0 is given) to obtain a correction value ΔVb3 which is subtracted from the initial set value Vb1 to calculate the third set value Vb3 thereby (Vb3=Vb1−ΔVb3, ΔVb3=C2×Rg2). The third set value Vb3, which is calculated as described above, is stored as the latest set value for the reference voltage for judgment Vb in a volatile area of the storage unit 13. That is, the set value of the reference voltage for judgment Vb in the storage unit 13 is updated to the third set value Vb3.

As a result, when this control routine is executed next time, the third set value Vb3, which is the latest reference voltage for judgment Vb stored in the storage unit 13, is adopted in the judging process in Step S101. Accordingly, the power generation amount monitoring process is started after providing such a state that the charge amount in the electricity accumulating unit 111 is low as compared with the initial state. Therefore, the frequency to request the power generating action is decreased by decreasing the frequency to perform the power generation amount monitoring process, for example, for an examinee having such a life habit that the body is frequently moved actively in many situations. Therefore, it is possible to mitigate the load of the examinee. In Step S114, if the latest value of the reference voltage for judgment Vb stored in the storage unit 13 is the third set value Vb3, it is unnecessary to dare to update the value of the reference voltage for judgment Vb. If the process of this step is completed, this routine is completed.

In Step S113, if it is judged that the average power generation rate Rga is not more than the second reference power generation rate Rg2 (Rga≤Rg2), it is possible to judge that the examinee (user) lives in accordance with an ordinary living pattern in which the power generation amount per unit time is average or ordinary. In this case, the routine proceeds to Step S115, and the reference voltage for judgment Vb is changed to the initial set value Vb1. The initial set value Vb1 is stored in the storage unit 13, and thus the set value of the reference voltage for judgment Vb in the storage unit 13 is updated to the initial set value Vb1. In Step S115, if the latest value of the reference voltage for judgment Vb stored in the storage unit 13 is the initial set value Vb1, it is unnecessary to dare to update the value of the reference voltage for judgment Vb. If the process of this step is completed, this routine is completed.

As described above, in this embodiment, the power generation amount monitoring process and the monitoring start condition regulating process are performed. Therefore, the excellent function and effect are obtained as described above. That is, it is possible to perform the appropriate process (warning operation and electric power supply from the emergency battery 112) depending on the power generation amount in the power generating unit 110 in the power generation amount monitoring process. For example, if the power generation rate Rg in the power generating unit 110 is lowered to an extent which cannot be affirmed to be sufficient, the power generation request warning is outputted from the warning unit 19 to hasten the examinee to perform the power generating action. Therefore, it is possible to expect the increase in the power generation amount in the power generating unit 110. If the power generation rate Rg in the power generating unit 110 is conspicuously lowered, the abnormality warning is outputted. Therefore, it is possible to inform people around the examinee of the abnormality of the examinee as well. In this procedure, the electric power is supplied from the emergency battery 112 to the electricity accumulating unit 111. Therefore, the electric power supply to the glucose sensor 4 is not stagnated or delayed.

In the monitoring start condition regulating process, it is possible to grasp and speculate the degree of the magnitude of the power generation amount per unit time in the living pattern (life habit) of the examinee. The setting of the execution start condition of the power generation amount monitoring process is adjusted on the basis of the result thereof. Therefore, the power generation amount monitoring process can be performed while considering the individual difference of the examinee more appropriately.

It is noted that the calculation expressions, which are usable to calculate the set value of the reference voltage for judgment Vb in Steps S112 and S114, are provided exemplarily by way of example. It is also allowable to use any other calculation method. The coefficients C1 and C2 may have different values, or they may have the same value. In the exemplary control described above, the three levels of the initial set value Vb1, the second set value Vb2, and the third set value Vb3 are prepared for the reference voltage for judgment Vb. However, there is no limitation thereto. For example, it is also allowable that a map, which represents the relationship between the reference voltage for judgment Vb and the average power generation rate Rga, is stored in the storage unit 13. The set value for the reference voltage for judgment Vb may be updated every time, by reading, from the map, the value of the reference voltage for judgment Vb corresponding to the average power generation rate Rga calculated every time when the control routine is performed.

Further, the same threshold value (first reference power generation rate Rg1) is exemplarily used for the judging processes in Steps S105 and S111 by way of example. However, there is no limitation thereto. This also holds in the same manner for the judging processes in Steps S107 and S113. It is noted that the following procedure is also available as a modified embodiment of this control routine. That is, if it is judged that the power generation rate Rg is higher than the first reference power generation rate Rg1 in the process in Step S105 (S105: No), then the judging process in Step S107 is omitted, and the process in Step S108 is performed as it is. In this embodiment, it is not necessarily indispensable that the power generation amount monitoring process and the monitoring start condition regulating process should be performed as a set. It is also possible to perform any one of the control processes singly.

Third Embodiment

Next, an explanation will be made about a third embodiment to carry out the present invention. In a measuring apparatus 1 according to this embodiment, a power generating unit 110 of an electric power supply device 11 is constructed to include a plurality of power generating devices. Except for this feature, the other basic components or parts are the same as or equivalent to those of the first and second embodiments. The power generation amount monitoring process in this embodiment has such a feature that the plurality of power generating devices are operated (started up), if necessary, depending on the monitoring result of the power generation amount in the power generating unit 110. The power generating devices concerning Examples 1 to 5 (piezoelectric element 110A, electromagnetic induction generator 110B, Seebeck element 110C, solar cell 110D, fuel cell 110E) can be adopted while being appropriately combined with each other for the plurality of power generating devices included in the power generating unit 110. A plurality of the power generating devices of the same type may be included in the power generating unit 110.

In this embodiment, the power generation control unit 32 of the control computer 3 further comprises a function to switch the electrical connecting relationship, i.e., the conduction and the shutoff between the electricity accumulating unit 111 and the respective power generating devices included in the power generating unit 110. The power generating device, which is included in the power generating devices included in the power generating unit 110 and which is in the conduction state with respect to the electricity accumulating unit 111 by the power generation control unit 32, is in the "operating state", and the power generating device, which is in the shut-off state, is in the "operation-stopped state".

Figure 13:
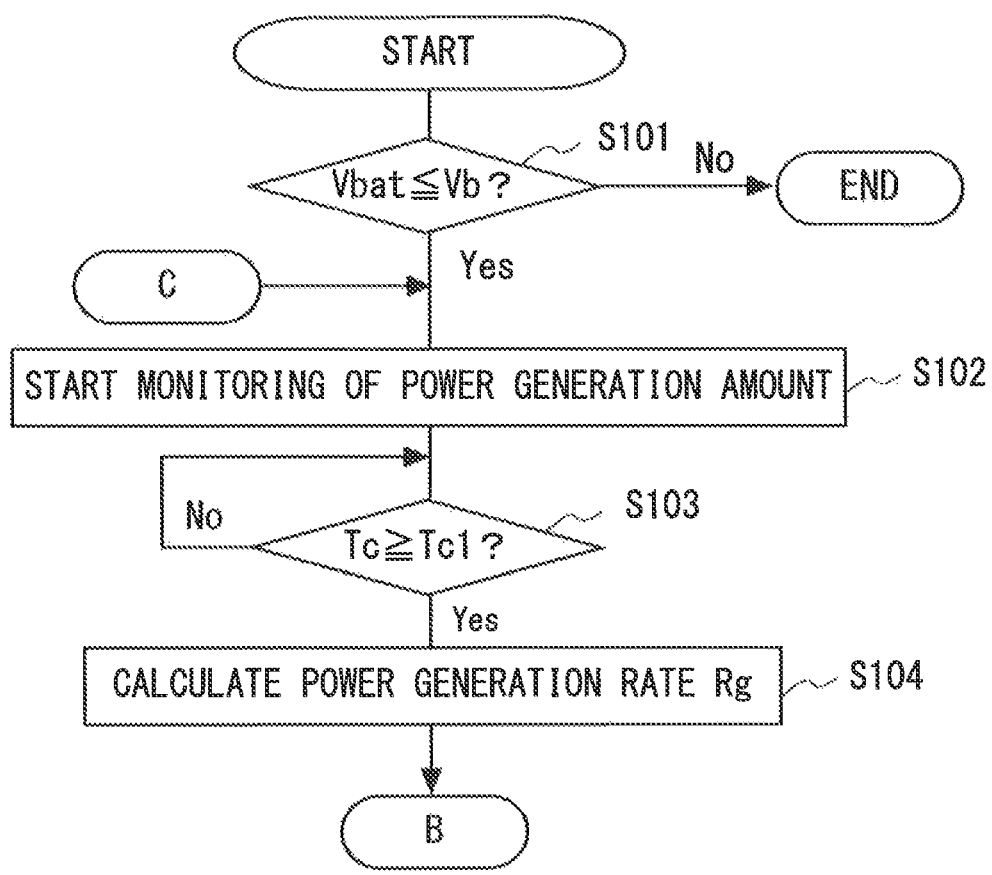
FIG. 13 shows a flow chart illustrating the process contents of a first half portion of a control routine in a third embodiment.
Figure 14:
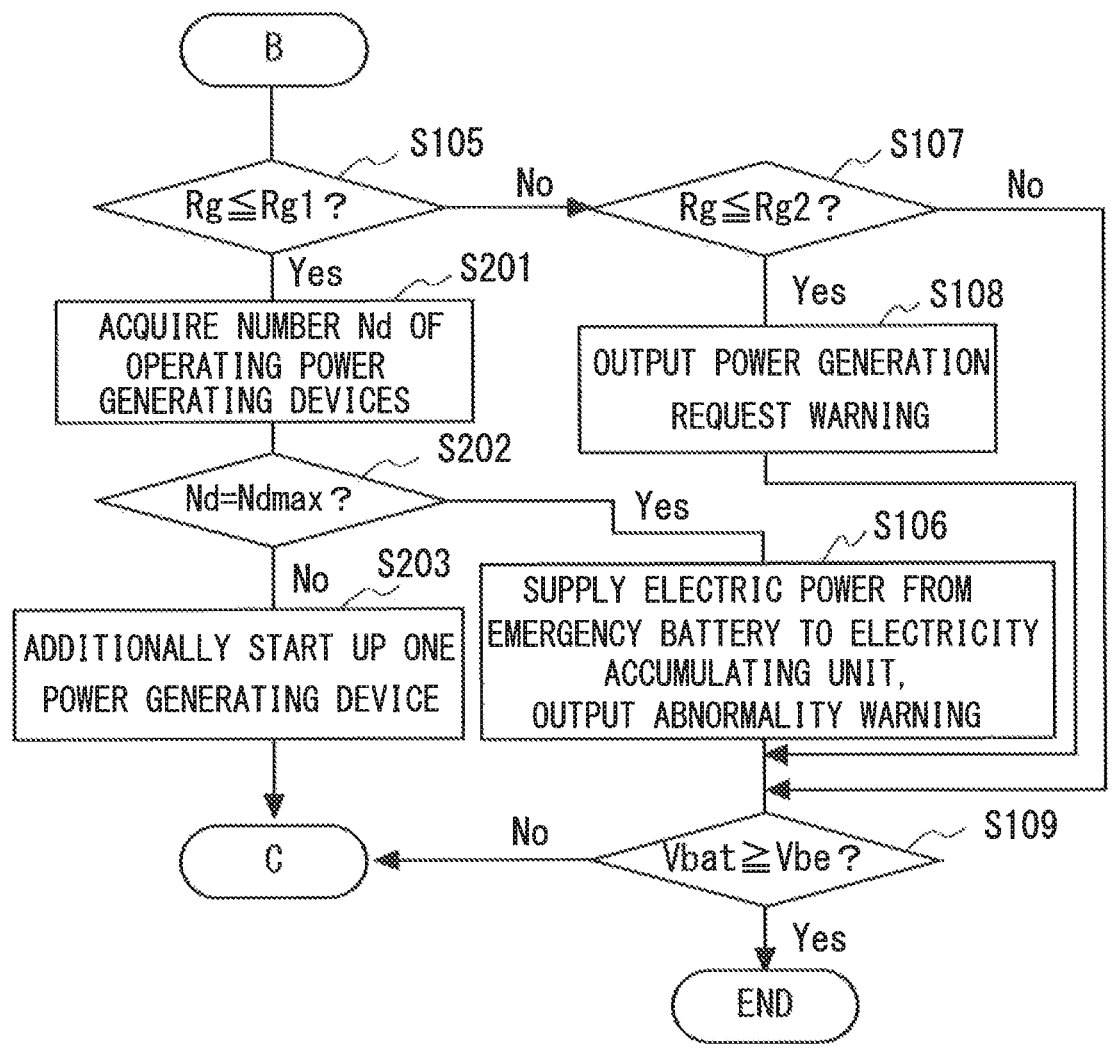
FIG. 14 shows a flow chart illustrating the process contents of a latter half portion of the control routine in the third embodiment.

FIGS. 13 and 14 show flow charts illustrating a control routine in the third embodiment. FIG. 13 shows the process contents of a first half portion of this control routine, and FIG. 14 shows the process contents of a latter half portion. In this control routine, the respective processes shown in the drawings are realized by developing the control programs stored in ROM to RAM by the control computer 3 and executing the control programs by the processor. This control routine is repeatedly executed every certain periods of time by the control computer 3 in a state in which the power source of the measuring apparatus 1 is turned ON. The steps, in which the same processes as those shown in FIGS. 11 and 12, are designated by the same reference numerals, any detailed explanation of which is omitted thereby.

In this control routine, the processes of Steps S101 to S105 are performed as having been already explained above. When the process of Step S104 shown in FIG. 13 is completed, the routine proceeds to Step S105 shown in FIG. 14 (see "B" shown in FIGS. 13 and 14). After proceeding to FIG. 14, if it is judged in Step S105 that the power generation rate Rg is not more than the first reference power generation rate Rg1 (Rg≤Rg1), the routine proceeds to Step S201. If it is judged that the power generation rate Rg is more than the first reference power generation rate Rg1 (Rg>Rg1), the routine proceeds to Step S107. The first reference power generation rate Rg1 is as described above. The process contents of Steps S107 and S108 are provided as having been already described above. If the affirmative judgment is made in Step S107 (Rg≤Rg2), the routine proceeds to Step S108. If the negative judgment is made (Rg>Rg2), the routine proceeds to Step S109. If the process of Step S108 is completed, the routine also proceeds to Step S109.

In Step S201, the control computer 3 (power generation control unit 32) acquires the number Nd of operating power generating devices as the number of power generating devices which are in the operating state by being allowed to be in conduction with the power generating unit 110. If the process of this step is completed, the routine proceeds to Step S202.

In Step S202, the control computer 3 (power generation control unit 32) judges whether or not the acquired number Nd of operating power generating devices is the maximum number Ndmax of operating devices. The maximum number Ndmax of operating devices is the number of power generating devices carried on the power generating unit 110. If the number Nd of operating power generating devices is the maximum number Ndmax of operating devices, it is shown that all of the power generating devices carried on the power generating unit 110 are in the conduction state with respect to the electricity accumulating unit 111 and all of the power generating devices are in the operating state. If it is judged in this step that the number Nd of operating power generating devices is smaller than the maximum number Ndmax of operating devices (S202: No), the routine proceeds to Step S203.

In Step S203, the control computer 3 (power generation control unit 32) additionally starts up one power generating device which is not operated at present and which is included in the power generating devices included in the power generating unit 110. In this procedure, the order of the power generating devices to be additionally started up can be set previously. For example, the type and the number of the power generating devices to be operated can be set previously in the initial setting upon the start of the measurement performed by the measuring apparatus 1. It is possible to expect the increase in the power generation amount to be brought about in future in the power generating unit 110 by increasing the number of operating power generating devices in this step.

If the process of Step S203 is completed, the routine returns to Step S102 shown in FIG. 13 after resetting the count of the power generation amount monitoring period Tc. If the routine returns to Step S102, the power generation control unit 32 continues the power generation amount monitoring process for the power generating unit 110 (see "C" shown in FIGS. 13 and 14).

On the other hand, if it is judged in Step S202 that the number Nd of operating power generating devices is the maximum number Ndmax of operating devices (Nd=Ndmax), it is impossible to additionally start up the power generating device any more. In this case, the routine proceeds to Step S106. The control routine 3 allows the emergency battery 112 to supply the electric power therefrom to the electricity accumulating unit 111, and the control computer 3 allows the warning unit 19 to output the abnormality warning. If the process of Step S106 is completed, the routine proceeds to Step S109.

In Step S109, as described above, it is judged whether or not the charging voltage Vbat in the electricity accumulating unit 111 is not less than the charge completion reference voltage Vbe. If it is judged that the charging voltage Vbat is lower than the charge completion reference voltage Vbe (Vbat<Vbe), then the routine returns to Step S102 shown in FIG. 13 after resetting the count of the power generation amount monitoring period Tc, and the power generation amount monitoring process is continued (see "C" shown in FIGS. 13 and 14). If it is judged in Step S109 that the charging voltage Vbat is not less than the charge completion reference voltage Vbe (Vbat≥Vbe), this routine is completed. In this case, the control computer 3 (power generation amount control unit 32) may complete this routine after the number of operating power generating devices in the power generating unit 110 is returned to the number provided in the initial setting.

Further, the monitoring start condition regulating process shown in FIG. 12 may be performed after the completion of this step. As described and noted in relation to the exemplary control in the second embodiment, it is also allowable to adopt the following procedure in the control routine according to this embodiment. That is, if it is judged that the power generation rate Rg is higher than the first reference power generation rate Rg1 in the process in Step S105 (S105: No), the routine proceeds to Step S108 as it is while omitting the judging process in Step S107.

The control in this embodiment will now be explained as exemplified by specified examples. For example, it is assumed that the power generating unit 110 of the measuring apparatus 1 is composed of the three power generating devices of the piezoelectric element 110A, the Seebeck element 110C, and the solar cell 110D. It is assumed that only the electricity accumulating unit 111 and the piezoelectric element 110A are in the operating state upon the start of the measurement to be performed by the measuring apparatus 1, and the other power generating devices (Seebeck element 110C, solar cell 110D) are set in the operation-stopped state. In this case, if it is judged that the number Nd of operating power generating devices is not the maximum number Ndmax of operating devices in Step S202 in the control routine (the number Nd of operating power generating device or devices is 1 or 2), for example, the Seebeck element 110C (solar cell 110D) is additionally started up (Step S203). The probability of increase in the power generation amount of the power generating unit 110 is raised by increasing the number of operating power generating devices, and the negative judgment tends to be made when the judging process concerning Step S105 is performed again. If the affirmative judgment is still made in Step S105, the solar cell 110D (Seebeck element 110C) is additionally started up in addition to the piezoelectric element 110A and the Seebeck element 110C (solar cell 110D). If the power generation rate Rg does not become higher than the first reference power generation rate Rg1 even when all of the power generating devices are operated as described above, the electric power is supplied from the emergency battery 112 to the electricity accumulating unit 111 (S106).

As described above, in the power generation amount monitoring process according to this embodiment, if the power generation amount produced by the power generating devices operating at present is small, it is possible to contemplate the increase in the total power generation amount in the power generating unit 110 by progressively increasing the number of operating power generating devices. If the power generation amount is still insufficient even when all of the power generating devices carried on the power generating unit 110 are operated, the electric power is supplied from the emergency battery 112 to the electricity accumulating unit 111. Therefore, it is possible to avoid such a situation that the electric power supply to the glucose sensor 4 is insufficient.

Fourth Embodiment

Next, an explanation will be made about a fourth embodiment for carrying out the present invention. In a measuring apparatus 1 according to this embodiment, a power generating unit 110 of an electric power supply device 11 is constructed to include a plurality of types of power generating devices based on different power generation systems. The plurality of types of power generating devices based on the different power generation systems can be specifically exemplified, for example, by the piezoelectric element 110A, the electromagnetic induction generator 110B, the Seebeck element 110C, the solar cell 110D, and the fuel cell 110E explained in Examples 1 to 5. In this embodiment, at least two or more types of the power generating devices of them are carried on the power generating unit 110. The other basic components of the measuring apparatus 1 are the same as or equivalent to those of the first to third embodiments.

The power generation control unit 32 of the control computer 3 controls and switches the "operating state" and the "operation-stopped state" by switching the conduction state and the shutoff state between the electricity accumulating unit 111 and the respective power generating devices included in the power generating unit 110 in the same manner as in the third embodiment. In this embodiment, if the power generation amount, which is produced by the power generating device or devices operated at present, is small in the power generation amount monitoring process, then the power generating device in operation is exchanged with another power generating device based on the different power generation system, and thus it is contemplated to increase the power generation amount in the power generating unit 110.

Figure 15:
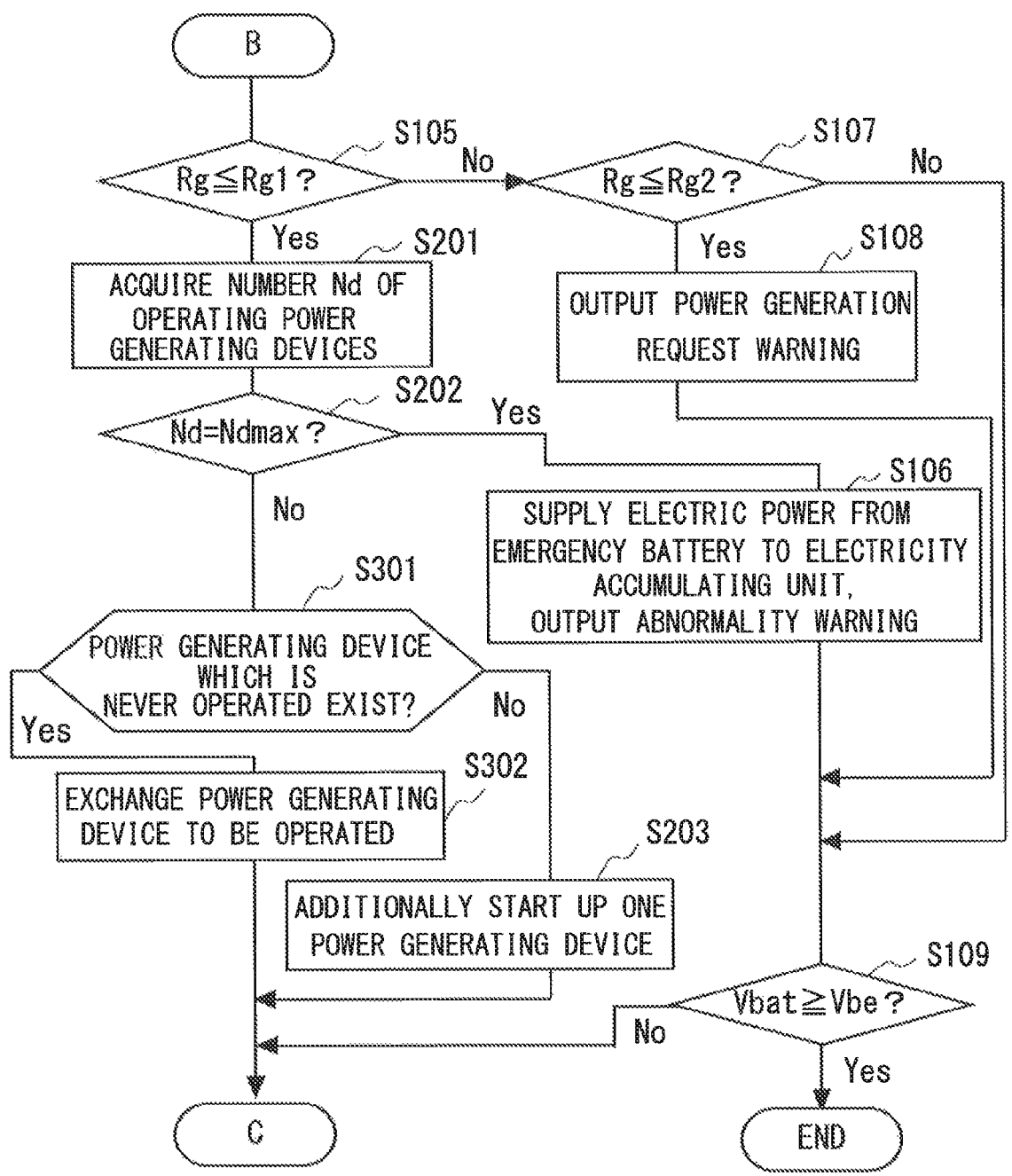
FIG. 15 shows a flow chart illustrating the process contents of a latter half portion of a control routine in the fourth embodiment.

The first half portion of the control routine in this embodiment is the same as or equivalent to that of the process flow shown in FIG. 13, for which FIG. 13 is cited or diverted. FIG. 15 shows a flow chart illustrating the process contents of a latter half portion of the control routine in the fourth embodiment. If the process in Step S104 shown in FIG. 13 is completed, the routine proceeds to Step S105 shown in FIG. 15

(see "B" shown in FIGS. 13 and 15). The steps, in which the same processes as those shown in FIG. 14 are performed in relation to the processes shown in FIG. 15, are designated by the same reference numerals, any detailed explanation of which is omitted thereby.

In Step S202 shown in FIG. 15, if it is judged that the number Nd of operating power generating devices is smaller than the maximum number Ndmax of operating devices (S202: No), the routine proceeds to Step S301. If it is judged that the number Nd of operating power generating devices is not smaller than the maximum number Ndmax of operating devices (S202: Yes), the routine proceeds to Step S106. The process contents of Step S106 have been already described, which are omitted from explanation in this section.

In Step S301, the control computer 3 (power generation control unit 32) judges whether or not any power generating device, which is never in the "operating state" after providing the present number Nd of operating power generating devices, exists. If the affirmative judgment is made in this step, the routine proceeds to Step S302. In Step S302, it is contemplated to increase the power generation amount in the power generating unit 110 by exchanging the power generating device in operation with any other power generating device which adopts any other power generation system. Specifically, the control computer 3 (power generation control unit 32) shuts off one power generating device in operation from the electricity accumulating unit 111, and one power generating device, which is selected from the power generating devices in the operation-stopped state, is allowed to be in conduction with the electricity accumulating unit 111. If the process of this step is completed, then the count of the power generation amount monitoring period Tc is reset, and the routine returns to Step S102 shown in FIG. 13 (see "C" shown in FIGS. 13 and 15). If the routine returns to Step S102, the power generation control unit 32 continues the monitoring of the power generation amount of the power generating unit 110.

On the other hand, if the negative judgment is made in Step S301, i.e., if it is judged that all of the power generating devices included in the power generating unit 110 have been already operated at least once after providing the present number Nd of operating power generating devices, then the routine proceeds to Step S203 (see FIG. 14). In Step S203, the control computer 3 (power generation control unit 32) additionally starts up one power generating device which is not operated at present and which is included in the power generating devices included in the power generating unit 110. It is possible to expect the increase in the power generation amount to be brought about in future in the power generating unit 110 by increasing the number of operating power generating devices in this step.

If the process of Step S203 is completed, the routine returns to Step S102 shown in FIG. 13 after resetting the count of the power generation amount monitoring period Tc. If the routine returns to Step S102, the power generation control unit 32 continues the power generation amount monitoring process for the power generating unit 110 (see "C" shown in FIGS. 13 and 15). For example, the processes of Steps S107 to S109 are the same as the processes shown in FIG. 14, any explanation of which is omitted in this section. The monitoring start condition regulating process shown in FIG. 12 may be performed after the completion of this routine.

The control in this embodiment will now be explained as exemplified by specified examples. For example, it is assumed that the power generating unit 110 of the measuring apparatus 1 is composed of the three power generating devices of the piezoelectric element 110A, the Seebeck element 110C, and the solar cell 110D. It is assumed that only the electricity accumulating unit 111 and the piezoelectric element 110A are in the operating state upon the start of the measurement to be performed by the measuring apparatus 1, and the other power generating devices (Seebeck element 110C, solar cell 110D) are set in the operation-stopped state. In the initial state as described above, if the affirmative judgment is made in Step S301, then the operation of the piezoelectric element 110A which is in operation at present is stopped in Step S302, and the Seebeck element 110C, for example, is started up in place thereof. If the power generation rate Rg does not become higher than the first reference power generation rate Rg1 yet even after the operation objective is exchanged in the power generating unit 110 from the piezoelectric element 110A to the Seebeck element 110C, the solar cell 110D is now started up in place of the Seebeck element 110C (Step S302). At this point in time, all of the power generating devices carried on the power generating unit 110 are operated at least once.

Therefore, if the process of Step S301 is subsequently performed, then the routine proceeds to S203 by providing the negative judgment, and the piezoelectric element 110A, for example, is additionally started up in addition to the solar cell 110D which is in operation at present. At this point in time, the number Nd of operating power generating device or devices is changed from 1 to 2. If the power generation rate Rg does not become higher than the first reference power generation rate Rg1 although the number Nd of operating power generating devices is increased as described above (S105: Yes), the power generating device, which is in operation at present, is exchanged with the power generating device which is in the operation-stopped state. For example, it is assumed that the solar cell 110D and the piezoelectric element 110A are in the operating state at present, and the Seebeck element 110C is in the operation-stopped state. On this assumption, the Seebeck element 110C is started up in place of the piezoelectric element 110A which is to be stopped. Accordingly, all of the power generating devices carried on the power generating unit 110 are operated at least once at this point in time, after the number Nd of operating power generating devices has the present value.

Therefore, if the negative judgment is still made in Step S301 next time, the piezoelectric element 110A, which is in the operation-stopped state, is additionally started up in addition to the solar cell 110D and the Seebeck element 110C which are in operation at present. At this point in time, all of the power generating devices carried on the power generating unit 110 are simultaneously operated. The number Nd of operating power generating devices is changed to the maximum number Ndmax of operating devices. If the power generation rate Rg is still low even in the state in which all of the power generating devices carried on the power generating unit 110 are operated as described above, the electric power is supplied from the emergency battery 112 to the electricity accumulating unit 111.

As described above, in the power generation amount monitoring process according to this embodiment, if the power generation amount, which is produced by the power generating device or devices operated at present, is small, the power generating device operated at present is exchanged with another power generating device based on the different power generation system so that the power generating device, which has the higher power generation efficiency in the present circumstance, is operated. Therefore, it is possible to contemplate the increase in the power generation amount in the power generating unit 110.

Fifth Embodiment

Next, an explanation will be made about a fifth embodiment for carrying out the present invention. In a measuring apparatus 1 according to this embodiment, a power generating unit 110 of an electric power supply device 11 is provided with a fuel cell 110E. As for the fuel cell 110E in this embodiment, the body fluid, which is, for example, blood or interstitial fluid of an examinee, is introduced into a fuel tank, and glucose contained therein is utilized as fuel. The body fluid as described above can be directly collected from blood vessel or cells in the body by adopting any known method. As for other features, the basic components of the measuring apparatus 1 are the same as or equivalent to those of the other embodiments. The electric power is generated by the fuel cell 110E in accordance with a power generation request command outputted from the control computer 3 to the electric power supply device 11.

Figure 16:
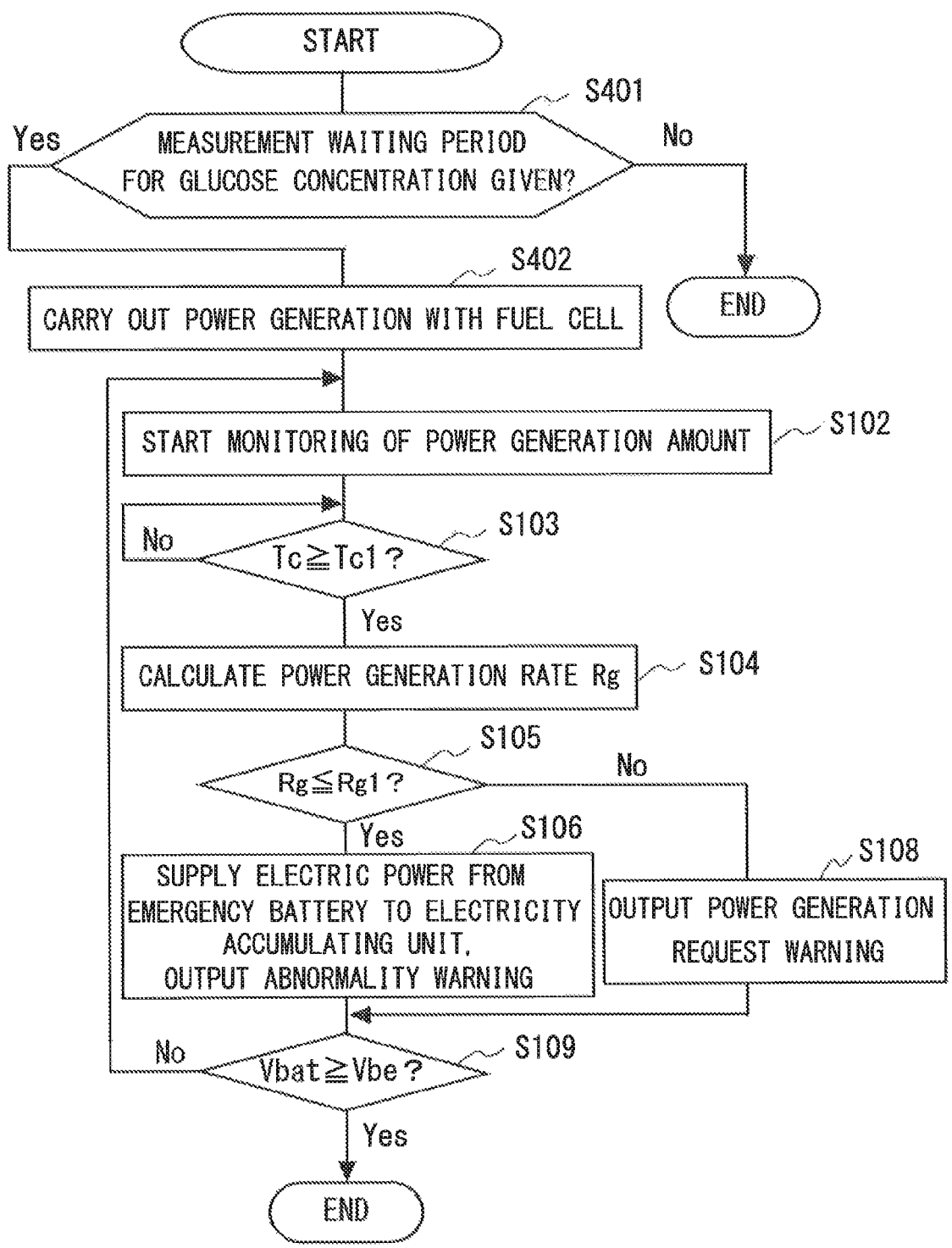
FIG. 16 shows a flow chart illustrating a control routine in a fifth embodiment.

FIG. 16 shows a flow chart illustrating a control routine in the fifth embodiment. In this control routine, the respective processes shown in the drawing are realized by developing the control programs stored in ROM to RAM by the control computer 3 and executing the control programs by the processor. This control routine is repeatedly executed every certain periods of time by the control computer 3 in a state in which the power source of the measuring apparatus 1 is turned ON.

When this control routine is started, the sensor control unit 12 of the control computer 3 judges whether or not the measurement waiting period, in which the routine waits for the measurement of the glucose concentration performed by the glucose sensor 4, is provided in Step S401. The measuring apparatus 1 is set so that the glucose concentration is measured periodically. The measurement period for measuring the glucose concentration and the measurement waiting period alternately arrive after starting the continuous measurement of the glucose concentration. If it is judged in this step that the present situation resides in the measurement period for the glucose concentration (S401: No), this routine is completed. If it is judged that the present situation resides in the measurement waiting period for the glucose concentration (S401: Yes), the routine proceeds to Step S402.

In Step S402, the control computer 3 outputs the power generation request command to the electric power supply device 11, and the power generation is carried out by using the fuel cell 110E. In this case, the power generating operation, which is performed by the fuel cell 110E, is carried out such that the body fluid, in which glucose as fuel is contained, is supplied to the anode layer 110E4 as described in Example 5. Therefore, if the measuring operation for measuring the glucose concentration by using the glucose sensor 4 is performed during the power generation carried out by the fuel cell 110E, it is feared that the measurement error of the glucose concentration may be increased and the measurement accuracy may be lowered. In view of the above, in this embodiment, the electric power is generated by the fuel cell 110E only during the measurement waiting period in which the glucose concentration is not measured.

After that, the power generation amount monitoring process is started (S102). If it is judged that the power generation amount monitoring period Tc is not less than the reference period Tc1 (S103: Yes), the power generation rate Rg is calculated (S104). If it is judged that the power generation rate Rg is not more than the first reference power generation rate Rg1 (S105: Yes), then the abnormality warning is outputted from the warning unit 19, and the electric power supply is carried out from the emergency battery 112 to the electricity accumulating unit 111 (S106). In this embodiment, the power generation is performed by using glucose in the body fluid as the fuel. Therefore, it is possible to judge that any conspicuously low power generation rate Rg indicates that an examinee may be highly possibly in hypoglycemia. Accordingly, in this embodiment, the abnormality warning is allowed to include the information of the contents to suggest that the examinee may be possibly in hypoglycemia. The process contents of Steps S108 and S109 have been already described with reference to FIG. 11, any explanation of which is omitted in this section.

In the case of the measuring apparatus 1 according to this embodiment, it is possible to appropriately judge whether or not the examinee is in hypoglycemia on the basis of the degree of the power generation amount (power generation rate Rg) brought about by the fuel cell 110E, even during the measurement waiting period in which the glucose concentration is not measured by the measuring apparatus 1. As described above, the power generating operation by the fuel cell 110E is not performed in the measurement period for measuring the glucose concentration. Therefore, it is possible to secure or guarantee the reliability of the measurement result obtained by using the glucose sensor 4.

In this embodiment, the monitoring start condition regulating process shown in FIG. 12 may be performed after the completion of the control routine shown in FIG. 16. When the measuring apparatus 1 of this embodiment is provided with the power generating devices of the other types including, for example, the piezoelectric element 110A, the Seebeck element 110C, and the solar cell 110D, in addition to the fuel cell 110E, if it is judged in Step S105 that the power generation rate Rg is not more than the first reference power generation rate Rg1, then the power generating device to be operated may be exchanged as explained in the fourth embodiment, and/or the power generating device in the operation-stopped state may be additionally started up in combination as well.

The embodiments of the present invention have been explained above. However, the measuring apparatus, the measuring system, the electric power supply apparatus, and the electric power supply method according to the present invention are not limited thereto. It is possible to include any combination thereof as far as possible.

DESCRIPTION OF THE REFERENCE SIGNS

1: glucose continuous monitoring (measuring) apparatus, 2: casing, 3: control computer, 4: electrochemical sensor (glucose sensor), 11: electric power supply device, 12: sensor control unit, 14: display unit component, 17: casing, 110: power generating unit, 111: electricity accumulating unit, 110A: piezoelectric element, 110B: electromagnetic induction generator, 110C: Seebeck element, 110D: solar cell, 110E: fuel cell.

The invention claimed is:

1. A measuring apparatus for measuring numerical information in relation to a test substance contained in a sample, the measuring apparatus comprising:
   a sensor configured to continuously generate a signal correlated with the numerical information in relation to the test substance contained in the sample;
   a power generating unit configured to generate an electric power for driving the sensor;
   an electricity accumulating unit charged by the electric power supplied from the power generating unit and configured to supply the accumulated electric power to the sensor;

a power generation control unit configured to monitor a power generation amount generated by the power generating unit and to calculate a power generation rate as the power generation amount per unit time in the power generating unit when the power generation amount generated by the power generating unit is monitored; and a storage unit configured to store the power generation rate calculated by the power generation control unit, wherein the power generation control unit is further configured to regulate a value of a reference voltage for judgment which is a threshold value to start the monitoring of the power generation amount generated by the power generating unit depending on an average power generation rate calculated by averaging values of the power generation rates obtained in a past plurality of times, including a most recently stored value of the power generation rates stored in the storage unit, and wherein the power generation control unit is configured to start a subsequent monitoring of the power generation amount in the power generating unit if a voltage value of the electric power accumulated in the electricity accumulating unit is not more than the reference voltage for judgment.

2. The measuring apparatus according to claim 1, further comprising:

a warning unit configured to output a predetermined warning if the power generation rate calculated by the power generation control unit is not more than a predetermined reference power generation rate.

3. The measuring apparatus according to claim 1, further comprising:

an emergency power source, wherein electric power is supplied from the emergency power source to the electricity accumulating unit if the power generation rate calculated by the power generation control unit is not more than a predetermined reference power generation rate.

4. The measuring apparatus according to claim 1, wherein:

the power generating unit is configured to include a plurality of power generating devices; and the power generation control unit is configured to increase a number of the power generating devices to be operated if the calculated power generation rate is not more than a predetermined reference power generation rate.

5. The measuring apparatus according to claim 1, wherein:

the power generating unit is configured to include a plurality of types of power generating devices based on different power generation systems; and the power generation control unit is configured to change the power generating device to be operated from the power generating device in operation to the power generating device of another type based on the different power generation system if the calculated power generation rate is not more than a predetermined reference power generation rate.

6. A measuring system for continuously measuring numerical information in relation to a test substance contained in a sample, the measuring system comprising:

a sensor configured to continuously generate a signal correlated with the numerical information in relation to the test substance contained in the sample;

a power generating unit configured to generate electric power for driving the sensor;

an electricity accumulating unit charged by the electric power supplied from the power generating unit and configured to supply the accumulated electric power to the sensor;

a power generation control unit configured to monitor a power generation amount generated by the power generating unit and to calculate a power generation rate as the power generation amount per unit time in the power generating unit when the power generation amount generated by the power generating unit is monitored; and a storage unit configured to store the power generation rate calculated by the power generation control unit, wherein the power generation control unit is further configured to regulate a value of a reference voltage for judgment which is a threshold value to start the monitoring of the power generation amount generated by the power generating unit depending on an average power generation rate calculated by averaging values of the power generation rates obtained in a past plurality of times, including a most recently stored value of the power generation rates stored in the storage unit, and wherein the power generation control unit is configured to start a subsequent monitoring of the power generation amount in the power generating unit if a voltage value of the electric power accumulated in the electricity accumulating unit is not more than the reference voltage for judgment.

7. An electric power supply apparatus for supplying electric power to a sensor for continuously generating a signal correlated with numerical information in relation to a test substance contained in a sample, the electric power supply apparatus comprising:

a power generating unit configured to generate the electric power for driving the sensor;

an electricity accumulating unit charged by the electric power supplied from the power generating unit and configured to supply the accumulated electric power to the sensor;

a power generation control unit configured to monitor a power generation amount generated by the power generating unit and to calculate a power generation rate as the power generation amount per unit time in the power generating unit when the power generation amount generated by the power generating unit is monitored; and a storage unit configured to store the power generation rate calculated by the power generation control unit, wherein the power generation control unit is further configured to regulate a value of a reference voltage for judgment which is a threshold value to start the monitoring of the power generation amount generated by the power generating unit depending on an average power generation rate calculated by averaging values of the power generation rates obtained in a past plurality of times, including a most recently stored value of the power generation rates stored in the storage unit, and wherein the power generation control unit is configured to start a subsequent monitoring of the power generation amount in the power generating unit if a voltage value of the electric power accumulated in the electricity accumulating unit is not more than the reference voltage for judgment.

8. An method for supplying electric power to a sensor for continuously generating a signal correlated with numerical information in relation to a test substance contained in a sample, the method comprising:

a step of generating the electric power for driving the sensor;

a step of monitoring a power generation amount generated in the generating step;

a step of performing charging with the electric power generated in the power generating step;

a step of supplying to the sensor the electric power accumulated in an electricity accumulating unit during the charging step;

a step of calculating a power generation rate as the power generation amount per unit time when the power generation amount generated is monitored;

a step of storing the power generation rate calculated in the calculating step;

a step of regulating a value of a reference voltage for judgment which is a threshold value to start the monitoring of the power generation amount depending on an average power generation calculated by averaging values of the power generation rates obtained in a past plurality of times, including a most recently stored value of the power generation rates, and a step of configuring a power generation control unit to start a subsequent monitoring of the power generation amount in the power generating unit if a voltage value of the electric power accumulated in the electricity accumulating unit is not more than the reference voltage for judgment.

* * * * *